United States Patent
Macor

(10) Patent No.: US 6,255,306 B1
(45) Date of Patent: *Jul. 3, 2001

(54) 4-INDOLE DERIVATIVES AS SEROTONIN AGONISTS AND ANTAGONISTS

(76) Inventor: John E. Macor, 235 E. 42nd St., Penfield, NY (US) 10017

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/132,170

(22) Filed: Aug. 11, 1998

Related U.S. Application Data

(63) Continuation of application No. 08/776,480, filed as application No. PCT/IB95/00335 on May 8, 1995, now abandoned, which is a continuation-in-part of application No. 08/281,192, filed on Jul. 26, 1994, now abandoned.

(51) Int. Cl.⁷ .................. A61K 31/496; A61K 31/4439; C07D 403/10; C07D 413/14; C07D 471/04

(52) U.S. Cl. .............................. 514/253.09; 514/253.03; 514/254.03; 514/254.09; 514/320; 514/323; 514/217.03; 514/217.08; 514/210.01; 514/414; 514/422; 544/361; 544/364; 544/367; 544/368; 544/373; 544/376; 540/596; 540/602; 546/201; 546/269.1; 548/466; 548/525; 548/950

(58) Field of Search .................................. 544/360, 362, 544/364, 361, 367, 368, 373; 514/254, 253.09, 254.09, 253.03, 254.03

(56) References Cited

U.S. PATENT DOCUMENTS

| 4,782,061 | * 11/1988 | Kruse et al. | 544/373 |
|---|---|---|---|
| 5,424,313 | * 6/1995 | Hartog et al. | 514/254 |
| 5,430,033 | * 7/1995 | Cliffe et al. | 514/254 |
| 5,723,464 | * 3/1998 | Brightwell et al. | 514/254 |

FOREIGN PATENT DOCUMENTS

| 189612 | * 8/1986 | (EP) . |
|---|---|---|
| 497512 | * 8/1992 | (EP) . |
| 313397 | * 6/1993 | (EP) . |
| 2097790 | * 11/1982 | (GB) . |
| 152655 | * 7/1986 | (JP) . |
| 91/18897 | * 12/1991 | (WO) . |
| 94/06769 | * 3/1994 | (WO) . |
| 9415919 | * 7/1994 | (WO) . |
| 96/03400 | * 2/1996 | (WO) . |

OTHER PUBLICATIONS

Duphar International, *Chemical Abstracts*, vol. 106, No. 5080 (Abstract for JP 61,152655, Jul. 11, 1986), 1987.*
Saxena, *Pharmac. Ther.* vol. 66, pp 339–368, 1995.*
Schoeffter et al., *European Journal of Pharmacology*, 244 p 251–257 (1993).*

* cited by examiner

*Primary Examiner*—Emily Bernhardt
(74) *Attorney, Agent, or Firm*—Peter C. Richardson; Paul H. Ginsburg; Seth H. Jacobs

(57) ABSTRACT

The present invention relates to compounds of the formula

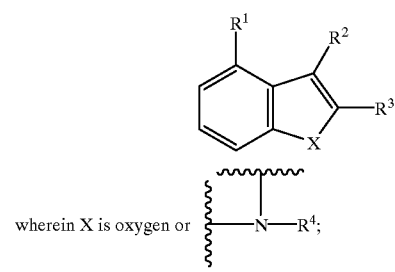

I wherein X is oxygen or 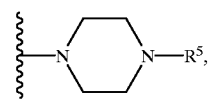

$R^1$ is a group of the formula

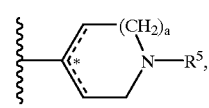

II

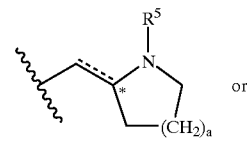

III

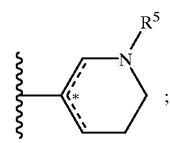

IV or

V

13 Claims, No Drawings

4-INDOLE DERIVATIVES AS SEROTONIN AGONISTS AND ANTAGONISTS

This application is a continuation of U.S. patent application Ser. No. 08/776,480, filed Jan. 23, 1997, now abandoned, which was a Section 371 National Stage filing of PCT/IB95/00335, filed May 8, 1995, which is a continuation-in-part of U.S. patent application Ser. No. 08/281,192, filed Jul. 26, 1994, now abandoned.

BACKGROUND OF THE INVENTION

The present invention relates to 4-indole derivatives, to processes and intermediates for their preparation, to pharmaceutical compositions containing them and to their medicinal use. The active compounds of the present invention are useful in treating or preventing disorders the treatment or prevention of which is facilitated by enhanced serotonergic neurotransmission.

U.S. Pat. No. 4,839,377, issued Jun. 13, 1989, and U.S. Pat. No. 4,855,314, issued Aug. 8, 1989, refer to 5-substituted 3-aminoalkyl indoles. The compounds are said to be useful for the treatment of migraine.

British Patent 2,035,310, published Jun. 18, 1980, refers to 3-aminoalkyl-1H-indole-5-thioamides and carboxamides. The compounds are said to be useful in treating hypertension, Raymond's disease and migraine.

European Patent Publication 303,506, published Jan. 15, 1989, refers to 3-poly:hydro-pyridyl-5-substituted-1H-indoles. The compounds are said to have 5-$HT_1$ receptor agonist and vasoconstrictor activity and to be useful in treating migraine.

European Patent Publication 354,777, published Feb. 14, 1990, refers to N-piperidinyl:indolyl:ethyl-alkane sulfonamide derivatives. The compounds are said to have 5$HT_1$ receptor agonist and vasoconstrictor activity and to be useful in treating cephalic pain.

European Patent Publication 438,230, published Jul. 24, 1991, refers to indole-substituted five-membered heteroaromatic compounds. The compounds are said to have 5-$HT_1$-like receptor agonist activity and to be useful in the treatment of migraine and other disorders for which a selective agonist of these receptors is indicated.

European Patent Publication 313,397, published Apr. 26, 1989, refers to 5-heterocyclic indole derivatives. The compounds are said to have exceptional properties for the treatment and prophylaxis of migraine, cluster headache, and headache associated with vascular disorders. These compounds are also said to have exceptional "5-$HT_1$-like" receptor agonism.

International Patent Publication WO 91/18897, published Dec. 12, 1991, refers to 5-heterocyclic indole derivatives. The compounds are said to have exceptional properties for the treatment and prophylaxis of migraine, cluster headache, and headache associated with vascular disorders. These compound are also said to have exceptional "5-$HT_1$-like" receptor agonism.

European Patent Publication 457,701 published Nov. 21, 1991, refers to aryloxy amine derivatives as having high affinity for 5-$HT_{1D}$ serotonin receptors. These compounds are said to be useful for treating diseases related to serotonin receptor dysfunction, for example, migraine.

European Patent Publication 497,512 A2, published Aug. 5, 1992, refers to a class of imidazole, triazole, and tetrazole derivatives which are selective agonists for 5-$HT_1$ like receptors. These compounds are said to be useful for treating migraine and associated disorders.

International Patent Publication WO 93/00086, published Jan. 7, 1993, describes a series of tetrahydrocarbazone derivatives as 5-$HT_1$ receptor agonists useful for the treatment of migraine and related conditions.

International Patent Publications WO 93/23396, published Nov. 25, 1993, refers to fused imidazole and triazole derivatives as 5-$HT_1$ receptor agonists for the treatment of migraine and other disorders.

P. Schoeffter et al. refer to methyl 4-{4-[4-(1,1,3-trioxo-2H-1,2-benzoisothiazol-2-yl)butyl]-1-piperazinyl}1H-indole-3-carboxylate as a selective antagonist for the 5-$HT_{1A}$ receptor in their paper "SDZ216-525, a selective and potent 5-$Ht_{1A}$ receptor antagonist" European Journal of Pharmacology, 244, 251–257 (1993).

International Patent Publication WO 94/06769, published Mar. 3, 1994, refers to 2-substituted-4-piperazine-benzothiophene derivatives that are serotonin 5-$HT_{1A}$ and 5-$HT_{1D}$ receptor agents useful in the treatment of anxiety, depression, migraine, stroke, angina and hypertension.

SUMMARY OF THE INVENTION

The present invention relates to compounds of the formula

I

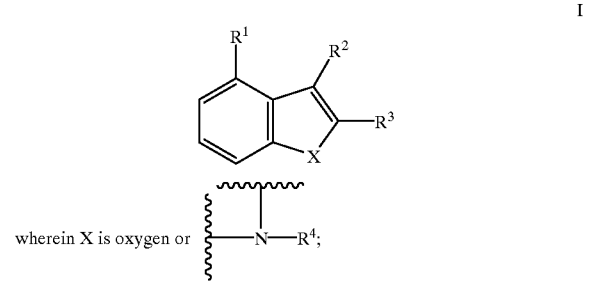

wherein X is oxygen or $R^1$ is a group of the formula

II

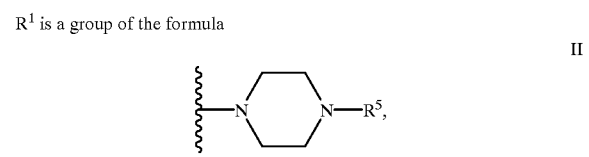

III

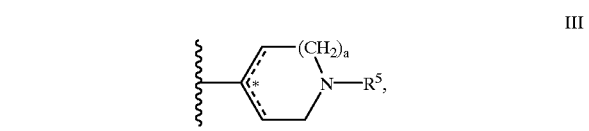

IV or

V

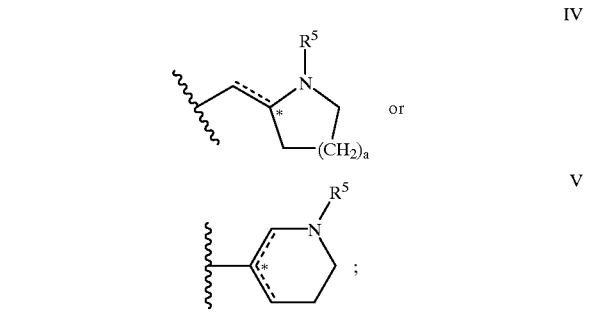

wherein X is oxygen or

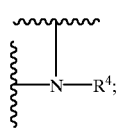

R¹ is a group of the formula

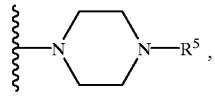
II

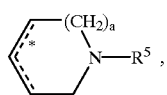
III

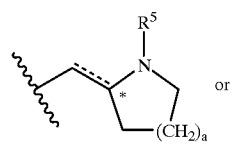
or
IV

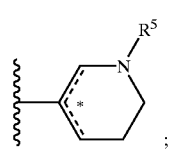
V

;

R² and R³ are independently selected from hydrogen, ($C_1$ to $C_6$)alkyl; ($C_1$ to $C_3$)alkylaryl; ($C_1$ to $C_3$)alkylheteroaryl, —NH(C=O)R⁶, —(C=O)NHR⁶, —O(C=O)R⁶, —(C=O)OR⁶, —(C=O)R⁶, OR⁶, —$SO_nR^6$, —$NHSO_nR^6$, —$SO_n$NHR⁶, aryl, and heteroaryl, with the proviso that R² and R³ are not both hydrogen; or R² and R³ may optionally be taken together to form a group of the formula —(C=O)NH—(CHR⁶)—$CH_2$—;

R⁴ is hydrogen, ($C_1$ to $C_3$)alkyl, —CHO, —(C=O)$CH_3$, and ($C_1$ to $C_3$)alkylaryl;

R⁵ is hydrogen, ($C_1$ to $C_3$)alkyl, or ($C_1$ to $C_3$)alkylaryl;

R⁶ is hydrogen, ($C_1$ to $C_6$)alkyl, ($C_1$ to $C_3$)alkylaryl, ($C_1$ to $C_3$)alkylheteroaryl, aryl, heteroaryl, and —($CH_2$)—Y—R⁷;

R⁷ is hydrogen, ($C_1$ to $C_6$)alkyl, ($C_1$ to $C_3$)alkylaryl, ($C_1$ to $C_3$)alkylheteroaryl, —(C=O)NHR⁸, —(C=O)OR⁸, —(C=O)R⁸, —OR⁸, —$SO_nR^8$, —$SO_n$NHR⁸, aryl, and heteroaryl;

R⁸ is hydrogen, ($C_1$ to $C_3$)alkyl, aryl, heteroaryl, ($C_1$ to $C_3$)alkylaryl and ($C_1$ to $C_3$)alkylheteroaryl;

Y is oxygen, —$SO_n$—, or NH;

a and n are independently 0, 1, or 2;

and said heteroaryl groups and the heteroaryl moieties of said alkylheteroaryl groups are selected from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4triazinyl, 1,2,3-triazinyl, 1,3,5triazinyl, 1,2,5-thiadiazinyl, 1,2,5-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl;

and said heteroaryl groups and the heteroaryl moieties of said alkylheteroaryl groups may optionally be substituted with from one to three substituents independently selected from ($C_1$ to $C_4$)alkyl, halogen (e.g., fluorine, chlorine bromine or iodine), hydroxy, cyano, carboxamido, nitro, ($C_1$ to $C_4$)alkoxy, ($C_1$ to $C_3$)alkylaryl, ($C_1$ to $C_3$)alkylheteroaryl, aryl, heteroaryl, and —($CH_2$)—Y—R⁷;

said aryl groups and the aryl moieties of said alkylaryl groups may optionally be substituted with one to three substituents independently selected from ($C_1$ to $C_4$)alkyl, halogen (e.g., fluorine, chlorine bromine or iodine), hydroxy, cyano, carboxamido, nitro, and ($C_1$ to $C_4$)alkoxy; and pharmaceutically acceptable salts thereof.

The compounds of formula I may have chiral centers and therefore may exist in different enantiomeric forms. This invention relates to all optical isomers and all stereoisomers of compounds of the formula I, and mixtures thereof. When R¹ is a group of the formula III, IV or V

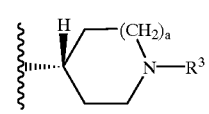
IIIa

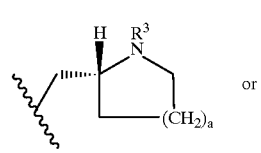
or
IVa

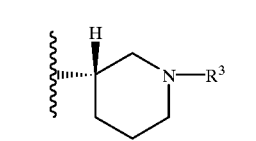
Va the R enantiomers (e.g., IIIa', IVa' and Va' as depicted above) at the chiral carbon designated by an asterisk in the ring in which "R¹" occurs are preferred. When R¹ is IIIa and "a" is one there is no chiral center.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to the pharmaceutically acceptable base salts of compounds of formula I. The bases which are used to prepare the pharmaceutically acceptable base salts of the aforementioned acid compounds of this invention are those which form non-toxic base salts, i.e., salts containing pharmaceutically acceptable cations, such as sodium, potassium, calcium and magnesium.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl, or be linear or branched and contain cyclic moieties.

Preferred compounds of the invention are compounds of the formula I wherein X is nitrogen; $R^2$ is hydrogen; $R^4$ is hydrogen and $R^5$ is hydrogen or —$CH_3$.

Other preferred compounds of the invention are those wherein X is nitrogen, $R^2$ and $R^3$ together form a ring of the formula —(C=O)NH—(CHR$^5$)—CH$_2$—.

The most preferred compounds of the invention are compounds of the formula I wherein $R^3$ is —(C=O)NHR$^5$, —(C=O)OR$^5$, heteroaryl, or $R^3$ together with $R^2$ forms a group of the structure —(C=O)NH—(CHR$^5$)—CH$_2$—; $R^4$ is hydrogen and $R^5$ is hydrogen or $CH_3$.

Examples of such compounds are the following:

4-(1-benzyl-pyrrolidin-3-yl)-2-(3-pyridin-3-yl-methyl-[1,2,4]oxadiazol-5-yl)-1H-indole;
4-(1-methyl-piperidin-4-yl)-1H-indole-2-carboxylic acid 4-chlorobenzylamide;
1-(2-(ethoxycarbonyl)-1H-indol-4-yl)-4-methylpiperazine;
4-methyl-1-(2-(pyrid-3-yl)-1H-indol-4-yl)piperazine;
1-(2-(3-cyanophenyl)-1H-indol-4-yl)-4-methylpiperazine;
5-(4-methylpiperazin-1-yl)-1-oxo-1,2,3,4-tetrahydro-9H-pyrido[3,4-b]indole;
1-(2-aminocarbonyl-1H-indol-4-yl)-4-methylpiperazine;
1-(2-carboxyl-1H-indol-4-yl)-4-methylpiperazine;
4-methyl-1-(2-phenylmethylaminocarbonyl-1H-indol-4-yl)piperazine;
4-methyl-1-(2-methyl-1H-indol-4-yl)piperazine;
1-[2-(2-(indol-3-yl)ethylaminocarbonyl)-1H-indol-4-yl]-4-methylpiperazine;
1-(3-formyl-2-methyl-1H-indol-4-yl)-4-methylpiperazine;
1-(2-(methoxycarbonyl)-1H-indol-4-yl)-4-methylpiperazine;
1-(2-(4-chlorophenylaminocarbonyl)-1H-indol-4-yl)-4-methylpiperazine;
1-(2-methyl-1H-indol-4-yl)piperazine;
1-(2-(4-chlorophenylmethylaminocarbonyl)-1H-indol-4-yl)-4-methylpiperazine;
4-methyl-1-(2-(pyrid-3-ylmethyl)aminocarbonyl-1H-indol-4-yl)piperazine;
4-methyl-1-(2-(pyrid-2-ylmethyl)aminocarbonyl-1H-indol-4-yl)piperazine;
4-methyl-1-(2-(pyrid-4-ylmethyl)aminocarbonyl-1H-indol-4-yl)piperazine;
1-(2-(ethoxycarbonyl)-1-methylindol-4-yl)-4-methylpiperazine;
1-(2-(4-chlorophenylmethylaminocarbonyl)-1-methylindol-4-yl)-4-methylpiperazine:
4-methyl-1-(2-(2-phenylethylaminocarbonyl)-1H-indol-4-yl)piperazine;
1-(2-(benzhydrylaminocarbonyl)-1H-indol-4-yl)-4-methylpiperazine;
4-methyl-1-(2-(1R-phenylethylaminocarbonyl)-1H-indol-4-yl)piperazine;
4-methyl-1-(2-(1S-phenylethylaminocarbonyl)-1H-indol-4-yl)piperazine;
4-methyl-1-(2-(methylaminocarbonyl)-1H-indol-4-yl)piperazine;
1-(2-(3,4-dichlorophenylmethylaminocarbonyl)-1H-indol-4-yl)-4-methylpiperazine;
1-(2-(4-chlorophenylmethoxycarbonyl)-1H-indol-4-yl)-4-methylpiperazine;
1-(2-(4-methoxyphenylmethoxycarbonyl)-1H-indol-4-yl)-4-methylpiperazine;
1-(2-(4-methoxyphenylmethylaminocarbonyl)-1H-indol-4-yl)-4-methylpiperazine;
1-(2-(4-fluorophenylmethylaminocarbonyl)-1H-indol-4-yl)-4-methylpiperazine;
4-methyl-1-(2-(4-trifluoromethylphenylmethoxycarbonyl)-1H-indol-4-yl)piperazine;
1-(2-(4-bromophenylmethylaminocarbonyl)-1H-indol-4-yl)-4-methylpiperazine;
1-(2-(4-aminosulfonylphenylmethylaminocarbonyl)-1H-indol-4-yl)-4-methylpiperazine;
1-(2-(4-butoxyphenylmethylaminocarbonyl)-1H-indol-4-yl)-4-methylpiperazine;
4-methyl-1-(2-(4-biphenylmethoxycarbonyl)-1H-indol-4-yl)piperazine;
4-methyl-1-(2-(4-phenylmethoxyphenylmethoxycarbonyl)-1H-indol-4-yl)piperazine;
1-(2-(4-ethoxyphenylmethoxycarbonyl)-1H-indol-4-yl)-4-methylpiperazine;
3-(4-chlorophenylmethyl)-5-(4-(4-methylpiperazin-1-yl)indol-2-yl)-1,2,4-oxadiazole;

and the pharmaceutically acceptable salts thereof.

Other compounds of the invention include:

4-methyl-1-(2-carboxyl-1H-indol-4-yl)piperazine;
4-methyl-1-(1H-indol-4-yl)piperazine;
4-methyl-1-(3-formyl-1H-indol-4-yl)piperazine; and
4-methyl-1-(2-carboxyl-1-methylindol-4-yl)piperazine.

The present invention also relates to a pharmaceutical composition for treating or preventing a condition selected from hypertension, depression, anxiety, eating disorders, obesity, drug abuse, cluster headache, migraine, pain, chronic paroxysmal hemicrania and headache associated with vascular disorders comprising an amount of a compound of the formula I or a pharmaceutically acceptable salt thereof effective in treating or preventing such condition and a pharmaceutically acceptable carrier.

The present invention also relates to a method for treating or preventing a condition selected from hypertension, depression, anxiety, eating disorders, obesity, drug abuse, cluster headache, migraine, pain, chronic paroxysmal hemicrania and headache associated with vascular disorders in a mammal, preferably a human, comprising administering to said mammal, requiring such treatment or prevention an amount of a compound of the formula I or a pharmaceutically acceptable salt thereof effective in treating or preventing such condition.

The present invention also relates to a method for treating or preventing a disorder the treatment or prevention of which is facilitated by enhanced serotonergic neurotransmission (e.g., depression, anxiety, eating disorders, obesity, drug abuse, cluster headache, migraine, pain, chronic paroxysmal hemicrania and headache associated with vascular disorders) in a mammal, preferably a human, comprising administering to said mammal, requiring such treatment or prevention an amount of a compound of the formula I or a pharmaceutically acceptable salt thereof effective in treating or preventing such condition.

The present invention also relates to a pharmaceutical composition for treating or preventing a disorder the treatment or prevention of which is facilitated by enhanced serotonergic neurotransmission (e.g., depression, anxiety, eating disorders, obesity, drug abuse, cluster headache, migraine, pain and chronic paroxysmal hemicrania and headache associated with vascular disorders) comprising an amount of a compound of the formula I or a pharmaceutically acceptable salt thereof effective in treating or preventing such condition and a pharmaceutically acceptable carrier.

The present invention relates to a pharmaceutical composition for treating or preventing disorders the treatment or prevention of which is facilitated by enhanced serotonergic neurotransmission in a mammal, preferably a human, comprising:

a) a pharmaceutically acceptable carrier;

b) a compound of the formula I or a pharmaceutically acceptable salt thereof; and c) a 5-HT re-uptake inhibitor, preferably sertraline, or a pharmaceutically acceptable salt thereof;

wherein the amounts of each active compound (e.g., the compund of formula I and the 5-HT re-uptake inhibitor) is such that the combination is effective in treating or preventing such condition.

The present invention also relates to a method for treating or preventing disorders the treatment or prevention of which is facilitated by enhanced serotonergic neurotransmission in a mammal, preferably a human, comprising administering to said mammal:

a) a compound of the formula I defined above, or a pharmaceutically acceptable salt thereof; and b) a 5-HT re-uptake inhibitor, preferably sertraline, or a pharmaceutically acceptable salt thereof;

wherein the amounts of each active compound (i.e., the compund of formula I and the 5-HT re-uptake inhibitor) is such that the combination is effective in treating or preventing such condition.

"Enhanced serotonergic neurotransmission", when used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (i.g., Vallium (trademark)). "Treating a chemical dependency," as used herein, means reducing or alleviating such dependency.

DETAILED DESCRIPTION OF THE INVENTION

In the description and reaction schemes which follow X, $R^1$, $R^2$, $R^3$, $R^4$, $R^5$, $R^6$, $R^7$, $R^8$, Y, a and n are as described above.

The compounds of formula I wherein $R^1$ is a group of the formula II can be prepared via the following reaction scheme:

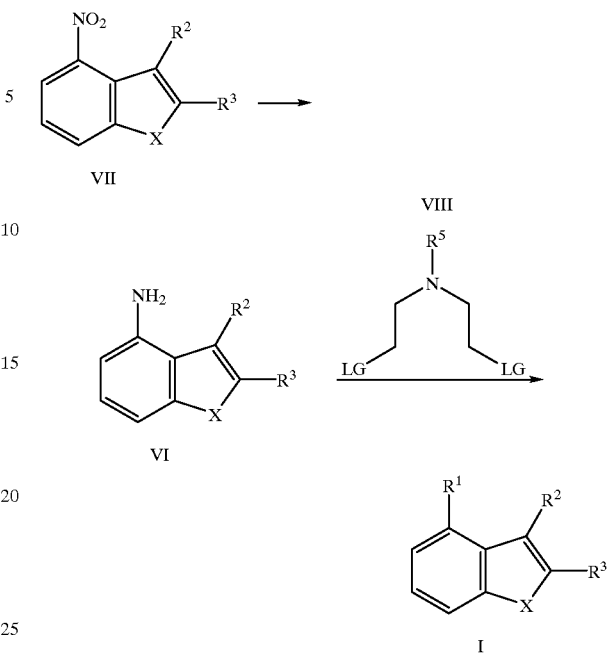

Compounds of formula VII are either commercially available or can be made by methods known to one skilled in the art. Compounds of formula VII, which are not commercially available can be prepared using methods known to one skilled in the art. For example, see *J. Am. Chem. Soc.*, 80, pages 4621–4622 (1958) for the synthesis of 4-nitroindole-2-carboxylates.

Compounds of formula VI can be prepared by the reduction of a compound of formula VII in an inert solvent. This reduction can be mediated either by transition metals or other metal reducing agents. When a transition metal mediates the reduction, a hydrogen source is also used. Suitable transition metals include palladium on carbon, palladium hydroxide on carbon, and platinum oxide. Palladium on carbon is preferred. Suitable hydrogen sources include hydrogen gas, ammonium formate, and formic acid. Hydrogen gas at a pressure of about one to about three atmospheres is the preferred hydrogen source. Three atmospheres of hydrogen gas is the preferred pressure. Suitable solvents include ($C_1$ to $C_4$) alcohols, acetonitrile, N,N-dimethylformamide, and N-methylpyrrolidine. Ethanol is the preferred solvent. Other metal reducing agents include iron sulfate ($FeSO_4$), Zinc (Zn) (metal) in aqueous hydrochloric acid, and Zn (metal) in aqueous hydrochloric acid. $FeSO_4$ is the preferred reducing agent of this group. Suitable solvents include aqueous ammonium hydroxide mixed with ethanol and concentrated aqueous hydrochloric acid. Aqueous ammonium hydroxide mixed with ethanol is the preferred solvent. All of the above reduction reactions are usually conducted at a temperature of from about 25° C. to about 100° C., preferably about 25° C. to about 50° C. It should be noted that compounds of formula II often can be used directly from the reduction reaction without chromatographic purification.

Compounds of formula I wherein $R^1$ is a group of the formula II can be prepared by the condensation reaction of a compound of formula VI with a compound of formula VIII wherein LG is an $S_n2$ leaving group such as chloro, bromo, iodo, $-OSO_2Ph$, $-OSO_2PhCH_3$, $-OSO_2CH_3$, $-OSO_2CF_3$ in an inert solvent in the presence of base. The preferred leaving group is iodo, prepared in situ from the chloro derivative using stiochiometric amounts of sodium iodide in the reaction mixture. Suitable solvents include ($C_1$ to $C_4$) alcohols, dimethyl sulfoxide, N,N-dimethylformamide, N-methylpyrrolidinone, acetonitrile, and acetone. Acetonitrile is the preferred solvent. Suitable bases include sodium hydroxide, potassium hydroxide, triethylamine, sodium carbonate, cesium carbonate, and sodium hydrogen carbonate. Sodium hydrogen carbonate is the preferred base. The reaction is usually conducted at a temperature of about 50° C. to about 154° C., preferably at about 56° C.

Compounds of formula I wherein $R^1$ is a group of the formula II can be converted into other compounds of formula I using methods known to one skilled in the art. For example, conversion of ethyl indole-2-carboxylates can be converted to indole-2-carboxylic acids by a variety of ester hydrolysis methodologies. The resulting carboxylic acids can be converted into new esters or amides using acid coupling methodologies known to one skilled in the art.

Compounds of formula I wherein $R^1$ is a group of the formula III, IV or V can be prepared as outlined via the following reaction scheme:

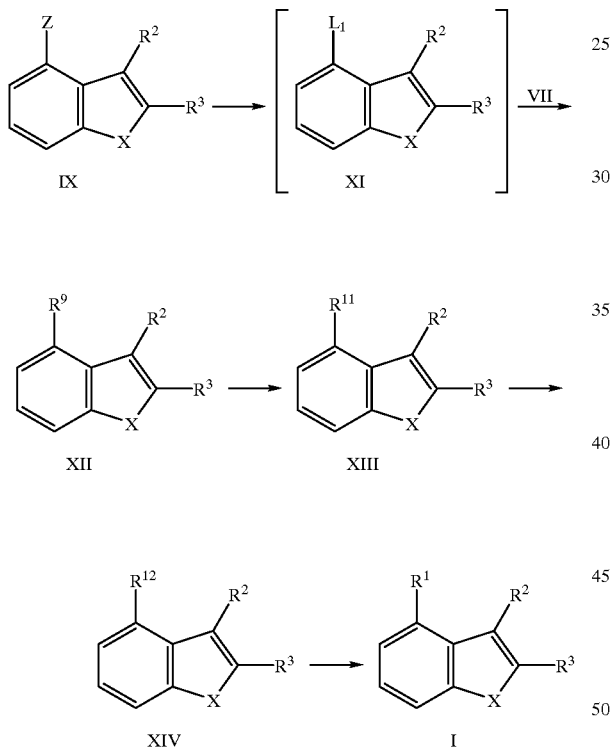

Compounds of formula XI can be prepared from compounds of formula IX, wherein Z is bromo or iodo, via a lithium/halogen exchange reaction of a compound of formula IX and an alkyllitium in an inert solvent. Compounds of formula XI are prepared in situ and are used directly with no isolation or purification. Suitable alkyllitium compounds include ($C_1$ to $C_5$) alkyllithium reagents including, for example, n-butyllithium, sec-butyllithium, and tert-butyllithium. The preferred alkyllithium compound is tert-butyllithium. Suitable inert solvents include ethers, such as tetrahydrofuran, 1,2-dioxane, diethyl ether, and dimethoxyethane. The preferred solvent is tetrahydrofuran. The reaction is generally run at a temperature of about −100° C. to about 25° C., preferably at a temperature of −78° C. to −40° C.

Compounds of formula XII, wherein $R^9$ is a group of the formula IIIa, IVa or Va as shown below:

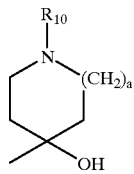

IIIa

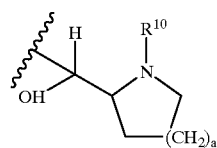

IVa

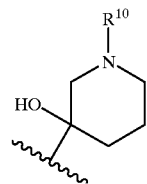

Va and $R^{10}$ is $R^5$ as defined above or a nitrogen protecting group as defined in *Protective Groups in Organic Synthesis,* T. W. Greene, John Wiley & Sons, New York (1981), pp. 218–287, are prepared via the condensation of compounds of formula XI with a ketone or aldehyde of the formula IIIb, IVb or Vb:

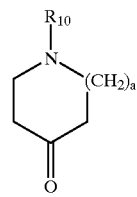

IIIb

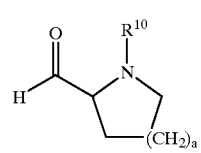

IVb

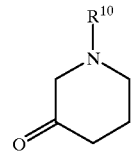

Vb in an inert solvent. Suitable inert solvents include ethers, such as tetrahydrofuran, 1,2-dioxane, diethyl ether, and dimethoxyethane. The preferred solvent is tetrahydrofuran. The reaction is generally run at a temperature of about −100° C. to about 25° C., preferably at a temperature of about −78° C. to −40° C.

Compounds of the formula XIII wherein $R^{11}$ is

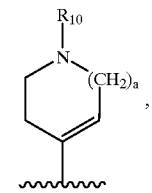  IIIc

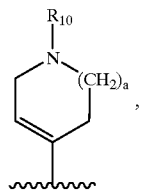  IIIc

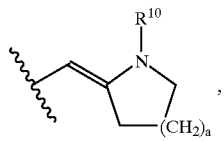  IVc

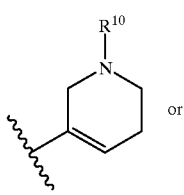  Vc

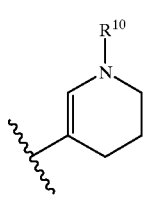  Vc' are prepared via the acid catalyzed dehydration of compounds of formula XII in an inert solvent. Suitable acid catalysts include minerals acids (such as hydrochloric acid), formic acid, acetic acid, proprionic acid, benzenesulfonic acid, p-toluenesulfonic acid, and trifluoromethanesulfonic acid. The preferred acid catalyst is p-toluenesulfonic acid. Suitable inert solvents include ethers such a 1,4-dioxane, diethyl ether, and tetrahydrofuran, ($C_1$ to $C_4$) alcohols, N,N-dimethylformamide, and chloroform. The preferred solvent is 1,4-dioxane. The reaction is generally run at a temperature of about 25° C. to about 125° C., preferably at a temperature of about 90° C. to 105° C.

Compounds of formula XII wherein $R^{10}$ is $R^5$ are compounds of formula I.

Compounds of the formula XIV wherein $R^{12}$ is

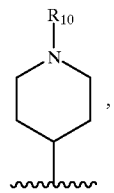  IIId

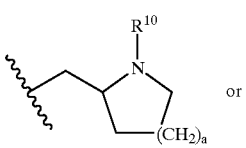  IVd

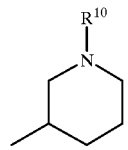  Vd and $R^{10}$ is defined as $R^5$ or a nitrogen protecting group as defined in *Protective Groups in Organic Synthesis*, T. W. Greene, John Wiley & Sons, New York (1981), pp. 218–287, are prepared via olefin hydrogenation of compounds of formula XIII using a transition metal catalyst and a hydrogen source in an inert solvent. Suitable transition metal catalysts include palladium on carbon, palladium hydroxide on carbon, tetrakis(triphenylphoshine)palladium(0). and rhodium (II) acetate. The preferred transition metal catalyst is palladium hydroxide on carbon. Suitable hydrogen sources include hydrogen gas, ammonium formate, and formic acid. The preferred hydrogen source is hydrogen gas, preferably used at a pressure of about one to about three atmospheres. Suitable inert solvents include ($C_1$ to $C_4$) alcohols, N,N-dimethylformamide, ethyl acetate, and acetic acid. The preferred solvent is 25% acetic acid in methanol. The reaction is generally run at a temperature of about 20° C. to about 75° C., preferably at a temperature of about 20° C. to 30° C.

Compounds of the formula XIV wherein $R^{10}$ is $R^5$ are compounds of the formula I.

Compounds of formula I wherein $R^5$ is hydrogen can be prepared by the deprotection of the nitrogen protecting group in a compound of the formula XIV wherein $R^{10}$ is defined as a nitrogen protecting group as defined in *Protective Groups in Organic Synthesis*, T. W. Greene, John Wiley & Sons, New York (1981), pp. 218–287. Methods of deprotection are defined for the different protecting in *Protective Groups in Organic Synthesis*, T. W. Greene, John Wiley & Sons, New York (1981), pp. 218–287, or are known to one skilled in the art.

Compounds of formula I wherein $R^5$ is hydrogen can be converted into other compounds of formula I by the alkylation of compounds of formula I wherein $R^5$ is hydrogen with a substrate of formula $R^{14}$-LG wherein $R^{14}$ is ($C_1$ to $C_3$) alkyl or ($C_1$ to $C_3$) alkylaryl and LG is a leaving group such as iodide, bromide, chloride, —$OSO_2$-phenyl, —$OSO_2$-p-tolyl, or —$OSO_2CF_3$ in the presence of a base an inert solvent. Suitable bases include sodium hydrogen carbonate, sodium carbonate, trialkylamines (including, for example, triethylamine), sodium, and sodium hydride. Triethylamine is the preferred base. Suitable solvents include ($C_1$ to $C_4$) alcohols, dioxane, diethyl ether, tetrahydrofuran, acetonitrile, N,N-dimethylformamide, and N-methylpyrrolidine. Ethanol is the preferred solvent. The reaction is usually conducted at a temperature of from about 25° C. to about 154° C., preferably about 70° C. to about 80° C.

Alternatively, compounds of formula I wherein $R^5$ is hydrogen can be converted into other compounds of formula I by reductive amination of compounds of formula I wherein $R^5$ is hydrogen with an aldehyde of formula $R^{15}CHO$, where $R^{15}$ is ($C_2$ to $C_3$) alkyl, ($C_2$ to $C_3$) alkylaryl using a transition metal catalyst and a hydrogen source in an inert solvent. Suitable catalysts include palladium on carbon, Raney nickel, platinum oxide, and palladium hydroxide on carbon. The preferred catalyst is palladium hydroxide on carbon. Suitable hydrogen sources include hydrogen gas, ammonium formate, and formic acid. Hydrogen gas at a pressure of about one to about three atmospheres is the preferred hydrogen source. Three atmospheres of hydrogen gas is the preferred pressure. Suitable solvents include ($C_1$ to $C_4$) alcohols, acetonitrile, N,N-dimethylformamide, and N-methylpyrrolidine. Ethanol is the preferred solvent. The reaction is usually conducted at a temperature of from about 25° C. to about 100° C., preferably about 25° C. to about 50° C.

Compounds of the formula IX, $R^{14}$-LG and $R^{15}CHO$ which are not commercially available can be made using methods known to one skilled in the art.

Compounds of formula I can be converted into other compounds of formula I using methods known to one skilled in the art. For example, conversion of ethyl indole-2-carboxylates can be converted to indole-2-carboxylic acids by a variety of ester hydrolysis methodologies. The resulting carboxylic acids can be converted into new esters or amides using acid coupling methodologies known to one skilled in the art.

Compounds of the formula I wherein $R^3$ is an ester of the formula —(C=O)$OR^6$ may be converted into (1,2,4)-oxadiazole derivatives according to the procedure in EP 438,230A2.

Unless indicated otherwise, the pressure of each of the above reactions is not critical. Generally, the reactions will be conducted at a pressure of about one to about three atmospheres, preferably at ambient pressure (about one atmosphere)

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)]salts.

Those compounds of the formula I which are also acidic in nature, e.g., where $R^2$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-$HT_1$) agonists and antagonists and may be used in the treatment of depression, anxiety, eating disorders, obesity, drug abuse, cluster headache, migraine, chronic paroxysmal hemicrania and headache associated with vascular disorders, pain, and other disorders arising from insufficient or deficient serotonergic neurotransmission. The compounds can also be used as centrally acting antihypertensives and vasodilators.

The affinities of the compounds of this invention for the various serotonin-1 receptors are evaluated using standard radioligand binding assays as described in the literature. The 5-$HT_{1A}$ affinity can be measured using the procedure of Hoyer et al. (Brain Res., 1986, 376, 85). The 5-$HT_{1C}$ affinity can be measured using the procedure of Pazos et al. (*Eur. J. Pharmacol.*, 1985, 106, 539). The 5-$HT_{1D}$ affinity can be measured using the procedure of Heuring and Peroutka (*J. Neurosci.*, 1987, 7, 894).

The in vitro activity of the compounds of the present invention at the 5-$HT_{1D}$ binding site may be determined according to the following procedure. Bovine caudate tissue may be homogenized and suspended in 20 volumes of a buffer containing 50 mM TRIS.hydrochloride (tris [hydroxymethyl]aminomethane hydrochloride) at a pH of 7.7. The homogenate may then be centrifuged at 45,000 G for 10 minutes. The supernatent can then be discarded and the resulting pellet resuspended in approximately 20 volumes of 50 mM TRIS.hydrochloride (HCl) buffer at pH 7.7. This suspension may then be pre-incubated for 15 minutes at 37° C. after which time the suspension may be centrifuged again at 45,000 G for 10 minutes and the supernatent should be discarded. The resulting pellet (approximately 1 g), may be resuspended in 150 ml of a buffer of 15 mM TRIS.hydrochloride (HCl) containing 0.01 percent ascorbic acid with a final pH of 7.7 and also containing 10 μM pargyline and 4 mM calcium chloride (CaCl$_2$). The suspension should be kept on ice at least 30 minutes prior to use.

The inhibitor. control or vehicle can then be incubated according to the following procedure. To 50 μl of a 20 percent dimethylsulfoxide (DMSO)/80 percent distilled water solution may be added 200 μl of tritiated 5-hydroxytryptamine (2 nM) in a buffer of 50 mM TRIS.hydrochloride containing 0.01 percent ascorbic acid at pH 7.7 and containing 10 μM pargyline and 4 μM calcium chloride, plus 100 nM of 8-hydroxy-DPAT (dipropylaminotetraline) and 100 nM of mesulergine. To this mixture may then be added 750 μl of bovine caudate tissue and the resulting suspension may be vortexed to ensure a homogenous suspension. The suspension can then be incubated in a shaking water bath for 30 minutes at 25° C. After incubation is complete, the suspension can be filtered using glass fiber filters (e.g., Whatman GF/B-filters™). The pellet can then be washed three times with 4 ml of a buffer of 50 mM TRIS.hydrochloride at pH 7.7. The pellet can then be placed in a scintillation vial with 5 ml of of scintillation fluid (aquasol 2, ™) and allowed to sit overnight. A percent inhibition can be calculated for each dose of the compound. An IC$_{50}$ value can then be calculated from the percent inhibition values.

The activity of the compounds of the present invention for 5-HT$_{1A}$ binding ability can be determined according to the following procedure. Rat brain cortex tissue can be homogenized and divided into samples of 1 g lots and diluted with 10 volumes of 0.32 M sucrose solution. The suspension may then be centrifuged at 900 G for 10 minutes and the supernate separated and recentrifuged at 70,000 G for 15 minutes. The supernate can be discarded and the pellet re-suspended in 10 volumes of 15 mM TRIS.hydrochloride at pH 7.5. The suspension should be allowed to incubate for 15 minutes at 37° C. After pre-incubation is complete the suspension should be centrifuged at 70,000 G for 15 minutes and the supernate discarded. The resulting tissue pellet may be resuspended in a buffer of 50 mM TRIS.hydrochloride at pH 7.7 containing 4 mM of calcium chloride and 0.01 percent ascorbic acid. The tissue should be stored at –70° C. until ready for an experiment. The tissue can be thawed immediately prior to use, diluted with 10 μm pargyline and kept on ice.

The tissue may then be incubated according to the following procedure. Fifty microliters of control, inhibitor, or vehicle (1 percent DMSO final concentration), may be prepared at various dosages. To this solution may be added 200 μl of tritiated DPAT at a concentration of 1.5 nM in a buffer containing 50 mM TRIS.hydrochloride at pH 7.7 containing 4 mM calcium chloride, 0.01 percent ascorbic acid and pargyline. To this solution may then be added 750 μl of tissue and the resulting suspension vortexed to ensure homogeneity. The suspension may then be incubated in a shaking water bath for 30 minutes at 37° C. The solution can then be filtered, washed twice with 4 ml of 10 mM TRIS.hydrochloride at pH 7.5 containing 154 mM of sodium chloride. The percent inhibition may be calculated for each dose of the compound, control or vehicle. An IC$_{50}$ value is calculated from the percent inhibition values.

The compounds of formula I of the present invention described in the following Examples were assayed for 5-HT$_{1A}$ and 5-HT$_{1D}$ affinity using the aforementioned procedures. All of the compounds that were tested had IC$_{50}$s of less than 0.60 μM.

The compounds of the invention can be tested for in vivo activity for antagonism of 5-HT$_{1D}$ agonist-induced hypothermia in Guinea Pigs according to the following procedure.

Male Hartley Guinea pigs from Charles River, weighing 250–275 grams on arrival and 300–600 g. at testing, serve as subjects in the experiment. The Guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneous (s.c.) prior to the 5-HT$_{1D}$ agonist, which is administered at a dose of 5.6 mg/kg, s.c. Before a first temperature reading is taken, each Guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at –90 minutes, the test compound is given at –60 minutes and an additional 30-minute reading is taken. The 5-HT$_{1D}$ agonist is then administered at 0 minutes and temperatures are taken 30, 60, 120 and 240 minutes later.

In subcutaneous screening experiments, a pre-drug baseline temperature reading is made at –30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

U.S. Pat. No. 4,536,518 describes the synthesis, pharmaceutical composition and use of sertraline for depression and is hereby incorporated by reference in its entirety. Sertraline hydrochloride has the chemical formula C$_{17}$H$_{17}$NCl$_2$ and the following structural formula

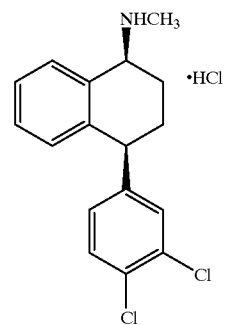

Its synthesis is described in U.S. Pat. No. 4,536,518, assigned to Pfizer Inc. Sertraline hydrochloride is useful as an antidepressant or an anorectic agent, and is also useful in the treatment of depression, chemical dependencies, anxiety-related disorders and premature ejaculation. U.S. Pat. No. 4,536,518 is hereby incorporated by reference in its entirety.

The compounds of formula I may advantageously be used in conjunction with one or more other therapeutic agents, for instance, different antidepressant agents such as tricyclic antidepressants (e.g. amitripyline, dothiepin, doxepin, trimipramine, butripyline, clomipramine, despramine, imipramine, iprindole, lofepramine, nortriptyline or protriptyline), monoamine oxidase inhibitors (e.g., isocarboxazid, pheneizine or tranylcyclopramine) or 5-HT re-uptake inhibitors (e,g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

5-HT re-uptake inhibitors, preferably sertraline, exihbit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

Preferably, the compounds of the formula I and the pharmaceutically acceptable salts thereof in combination with a 5-HT re-uptake inhibitor (e.g., fluvoxamine, sertraline, fluoxetine or paroxetine), preferably sertraline, or a pharmaceutically acceptable salt or polymorph thereof (herein, the combination of a compound of formula I with a 5-HT re-uptake inhibitor is collectively referred to as "the active combination") are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced Parkinsonism and tardive dyskinesias), endocrine disorders (e,g., hyperprolactinaemia), vasospasm (particularly in the cerebral vasculature), gastrointestinal tract disorders (where changes in motility and secretion are involved) and chronic paroxysmal hemicrania and headache associated with vascular disorders.

The active compounds of the invention can be evaluated as anti-migraine agents by testing the extent to which they mimic sumatriptan in contracting the dog isolated saphenous vein strip [P. P. A. Humphrey et al., Br. J. Pharmacol., 94, 1128 (1988)]. This effect can be blocked by mathiothepin, a known serotonin antagonist. Sumstriptan is known to be useful in the treatment of migraine and produces a selective increase in carotid vascular resistance in the anesthetized dog. The pharmacological basis of sumatriptan efficacy has been discussed in W. Fenwick et al., Br. J. Pharmacol., 96, 83 (1989).

The serotonin 5-HT, agonist activity can be determined by the in vitro receptor binding assays as described for the 5-HT$_{1A}$ receptor using rat cortex as the receptor source and [$^3$H]-8-OH-DPAT as the radioligand [D. Hoyer et al. Eur. J. Pharm., 118, 13 (1985)] and as described for the 5-HT$_{1D}$ receptor using bovine caudate as the receptor source and [$^3$H]serotonin as the radioligand [R. E. Heuring and S. J. Peroutka, J. Neuroscience, 7, 894 (1987)]. Of the active compounds tested, all exhibited an IC$_{50}$ in either assay of 250 nM or less.

Activity of the active combination as antidepressants and related pharmacological properties can be determined by methods (1)–(4) below, which are described in Koe, B. et al., Journal of Pharmacology and Experimental Therapeutics, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbid acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage. The compounds of this invention may exist in different polymorphic forms, i.e., different crystalline forms.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg. to about 2000 mg., preferably from about 0.1 mg. to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg. to about 2000 mg., preferably from about 1 mg. to about 200 mg. of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 μg to about 1000 μg of the active compound of this invention, preferably from about 1 μg. to about 10 mg. of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg. to about 2000 mg. of a 5-HT re-uptake inhibitor, preferably sertraline, preferably from about 1 mg. to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg. to about 100 mg. per kg. of body weight per day of a 5-HT re-uptake inhibitor, preferably sertraline, preferably from about 0.1 mg. to about 10 mg. per kg. of body weight per day of sertraline; with from about 0.001 mg. to about 100 mg. per kg. of body weight per day of a compound of formula I, preferably from about 0.01 mg. to about 10 mg. per kg. of body weight per day of a compound of formula I, although variations will necessarily occur depending upon the conditions of the subject being treated and the particular route of administration chosen.

The following Examples illustrate the preparation of the compounds of the present invention. Commercial reagents were utilized without further purification. Melting points are uncorrected. NMR data are reported in parts per million (δ) and are referenced to the deuterium lock signal from the sample solvent. Specific rotations were measured at room temperature using the sodium D line (589 nm). Unless otherwise stated, all mass spectrum were performed using electron impact (EI, 70 eV) conditions. Chromatography refers to column chromatography performed using 32–63 μm silica gel and executed under nitrogen pressure (flash chromatography) conditions. Room temperature refers to 20–25° C.

EXAMPLE 1

General Conversion of 4-Nitroindoles to 1-(Indol-4-yl)piperazines

A mixture of the 4-nitroindole (10.0 mmol), 10% palladium on carbon (20% by weight), and absolute ethanol (50 mL) was shaken under a hydrogen atmosphere (3 atm) for 2 hours. The resulting reaction mixture was filtered through Celite®, and the filtrate was evaporated under reduced pressure to afford the corresponding 4-aminoindole, which was used directly (assumed 100% yield) in the next step below.

To a stirred solution of the 4-aminoindole (10.0 mmol assumed from above) in anhydrous acetonitrile (100 mL) was added (in order) sodium hydrogen carbonate (3.36 g, 40.0 mmol, 4.0 equivalents), sodium iodide (3.00 g, 20.0 mmol, 2.0 equivalents), and mechlorethamine hydrochloride (1.93 g, 10.0 mmol, 1.0 equivalent). The resulting reaction mixture was heated at reflux under nitrogen overnight (16 hours). The resulting reaction mixture was then evaporated under reduced pressure, and the residue was partitioned between a saturated solution of sodium hydrogen carbonate (50 mL) and ethyl acetate (50 mL). The organic layer was removed, and the aqueous layer was extracted with ethyl acetate (3×50 mL). The organic extracts were combined, dried (magnesium sulfate), and evaporated under reduced pressure. The residue was column chromatographed using silica gel (approximately 150 g) and elution with an appropriate solvent system to afford the title compound.

Using the above procedure, the following compounds were prepared:

A. 1-(2-(Ethoxycarbonyl)-1H-indol-4-yl)-4-methylpiperazine

Ethyl 4-nitroindole-2-carboxylate [*J. Am. Chem. Soc.*, Vol.80, pages 4621–4622 (1958)] was used. Chromatography using elution with 20:1:0.1 [methylene chloride/methanol/amonium hydroxide] afforded the title compound (69%) as an off-white foam: $^1$H NMR (DMSO-$d_6$) δ7.19–7.09 (m, 3H), 6.54 (dd, J=1.3 and 6.9 Hz, 1H), 4.34 (q, J=7.1 Hz, 2H), 3.29 (br t, 4H), 3.20 (br t, 4H), 2.73 (s, 3H), 1.34 (t, J=7.1 Hz, 3H); LRMS (m/z, relative intensity) 288 (10), 287 (M$^+$, 59), 272 (5), 217 (25), 170 (34), 158 (41), 85 (95), 83 (100); HRMS calculated for $C_{16}H_{21}N_3O_2$ 287.1635, found 287.1599.

Analytical calculated for $C_{16}H_{21}N_3O_2 \cdot 0.70$ $CH_2Cl_2$: C, 57.84; H, 6.51; N, 12.12. Found: C, 57.98; H, 6.63; N, 12.07.

B. 4-Methyl-1-(2-(pyrid-3-yl)-1H-indol-4-yl)piperazine

4-Nitro-2-(pyrid-3-yl)indole was used. Chromatography using elution with 10:1:0.1 [methylene chloride/methanol/amonium hydroxide] afforded the title compound (2%) as a brown oil: $^1$H NMR (CD$_3$OD) δ8.92 (d, J=1.8 Hz, 1H), 8.39 (dd, J=1.5 and 4.7 Hz, 1H), 8.21–8.16 (m, 1H), 7.50–7.43 (m, 2H), 6.99 (s, 1H), 6.88–6.83 (m, 2H), 4.90 (s, NH exchangeable), 3.20 (br t, 4H), 2.66 (br t, 4H), 2.37 (s, 3H): FAB LRMS (m/z, relative intensity) 294 (26), 293 (MH$^+$, 100).

C. 1-(2-(3-Cyanophenyl)-1H-indol-4-yl)-4-methylpiperazine 3-(3-Cyanophenyl)-4-nitroindole was used. Chromatography using elution with 10:1:0.1 [methylene chloride/methanol/amonium hydroxide] afforded the title compound (30%) as a pale red solid: $^{13}$C NMR (CD$_3$OD) δ152.3, 148.5, 141.5, 135.0, 130.8, 129.8, 129.5, 127.5, 126.6, 125.8, 120.7, 109.6, 107.9, 102.9, 55.0, 54.9, 44.0.

D. 5-(4-Methylpiperazine-1-yl)-1-oxo-1,2,3,4-tetrahydro-9H-pyrido[3,4-b]indole 5-Nitro-1-oxo-1,2,3,4-tetrahydro-9H-pyrido[3,4-b]indole was used. Chromatography using elution with 10:1:0.1 [methylene chloride/methanol/amonium hydroxide] afforded the title compound (56%) as an off-white amorphous solid: LRMS (m/z, relative intensity) 285 (53), 284 (M$^+$, 100), 269 (7), 240 (16), 214 (59); HRMS calculated for $C_{16}H_{20}N_4O$ 284.1639, found 284.1610.

E. 4-Methyl-1-(2-methyl-1H-indol-4-yl)piperazine

2-Methyl-4-nitroindole was used. Chromatography using elution with 10:1:0.1 [methylene chloride/methanol/amonium hydroxide] afforded the title compound (88%) as an off-white solid: mp, 178–180° C.; $^{13}$C NMR (DMSO-$d_6$) δ142.7, 137.1, 134.1, 121.4, 120.5, 106.1, 105.9, 97.8, 53.4, 48.2, 42.9, 13.4; LRMS (m/z, relative intensity) 229 (M$^+$, 100), 214 (9), 185 (11), 159 (59), 144 (21), 130(29), 71 (16); HRMS calculated for $C_{14}H_{19}N_3$ 229.1581, found 229.1561.

F. 1-(2-(Ethoxycarbonyl)-1-methyl-1H-indol-4-yl)-4-methylpiperazine

Ethyl 1-methyl-4-nitroindole-2-carboxylate was used. Chromatography using elution with 15:1:0.1 [methylene chloride/methanol/amonium hydroxide] afforded the title compound (35%) as an amorphous off-white solid: $^1$H NMR (CDCl$_3$) δ7.25 (t, J=8.0 Hz, 1H), 7.18 (s, 1H), 7.09 (d, J=8.5 Hz, 1H), 6.62 (d, J=7.4 Hz, 1H), 4.37 (q, J=7.1 Hz, 2H), 4.05 (s, 3H), 3.60 (br t, J=4.9 Hz, 4H), 3.23 (br t, 4H), 2.74 (s, 3H), 1.41 (t, J=7.1 Hz, 3H); FAB LRMS (m/z, relative intensity) 303 (36), 302 (MH$^+$, 100), 288 (5); HRMS calculated for $C_{17}H_{23}N_3O_2$ 301.1792, found 301.1802.

EXAMPLE 2

General Procedure for the Conversion of Indole-2-carboxylic acids to Indole-2-carboxylates and Indole-2-carboxamides To a stirred solution of 4-(4-methylpiperazin-1 yl)indole-2-carboxylic acid (0.259 g, 1.00 mmol) in anhydrous N,N-dimethylformamide (6 mL) at room temperature was added carbonyldiimidazole (0.574 g, 2.00 mmol, 2.0 equivalents). The resulting reaction solution was stirred at room temperature under nitrogen for 2 hours. Then, the appropriate amine (4.00 mmol, 4.0 equivalents) or alcohol (4.00 mmol, 4.0 equivalents) was added directly, and the resulting reaction solution was stirred at room temperature under nitrogen overnight. In the case of alcohols, sodium hydride (60% in oil, 0.160 g, 4.00 mmol, 4.0 equivalents) was added, and the resulting reaction was heated an additional 2 hours at 50° C. The reaction solution was then evaporated under reduced pressure, and redissolved in chloroform (5 mL). Undissolved solid was removed via filtration through Celite®, and the filtrate was evaporated under reduced pressure. The residue was column chromatographed using silica gel (approximately 50 g) and elution with an appropriate solvent system to afford the corresponding indole-2-carboxamide or indole-2-carboxylate.

Using the above procedure, the following compounds were prepared:

A. 1-(2-Aminocarbonyl-1H-indol-4-yl)-4-methylpiperazine

Ammonia was the amine used. Chromatography using elution with methylene chloride/methanol/ammonium hydroxide [10:1:0.1] afforded the title compound (78%) as a white solid: mp, 220–221° C.; $^{13}$C NMR (acetone-$d_6$) δ164.0, 147.8, 138.9, 130.5, 125.3, 122.3, 107.1, 107.0, 103.1, 56.2, 51.9, 46.3; LRMS (m/z, relative intensity) 258

($M^+$, 63), 241 (10), 188 (10), 170 (22), 68 (100); HRMS calculated for $C_{14}H_{18}N_4O$ 258.1482, found 258.1472.

B. 4-Methyl-1-(2-phenylmethylaminocarbonyl-1H-indol-4-yl)piperazine

Benzylamine was the amine used. Chromatography using elution with methylene chloride/methanol/ammonium hydroxide [15:1:0.1] afforded the title compound (72%) as an amorphous white foam: mp, 102–103° C.; $^{13}C$ NMR (acetone-$d_6$) δ162.1, 147.8, 140.5, 138.9, 130.7, 129.1, 128.3, 127.6, 125.2, 122.3, 107.2, 107.1, 102.2, 56.2, 51.9, 46.3, 43.4; LRMS (m/z, relative intensity) 349 (21), 348 ($M^+$, 100), 278 (18), 258 (34), 241 (16), 91 (25); HRMS calculated for $C_{21}H_{24}N_4O$ 348.1952, found 348.1943.

Analytical calculated for $C_{21}H_{24}N_4O.1.1$ water: C, 68.49; H, 7.17; N, 15.21. Found: C, 68.28; H, 7.42; N, 15.55.

C. 1-[2-(2-(Indol-3-yl)ethylaminocarbonyl)-1H-indol-4-yl]-4-methylpiperazine Tryptamine was the amine used. Chromatography using elution with methylene chloride/methanol/ammonium hydroxide [10:1:0.1] afforded the title compound (76%) as an amorphous white solid: mp, 128–129° C.; $^{13}C$ NMR ($CD_3OD$) δ164.0, 147.5, 139.6, 138.2, 131.0, 128.9, 125.8, 123.5, 122.6, 122.3, 119.6, 119.4, 113.4, 112.2, 108.0, 107.8, 103.3, 56.3, 52.1, 46,2, 41.8, 26.5; LRMS (m/z, relative intensity) 401 ($M^+$, 7), 348 (14), 186 (27), 130 (100); HRMS calculated for $C_{24}H_{27}N_5O$ 401.2218, found 401.2213.

Analytical calculated for $C_{24}H_{27}N_5O.0.5$ ammonium hydroxide [ammonium hydroxide]. 0.5 water: C, 67.34; H, 7.18; N, 18.00. Found: C, 67.76; H, 6.98; N, 18.07.

D. 1-(2-(4-Chlorophenylaminocarbonyl)-1H-indol-4-yl)-4-methylpiperazine p-Chloroaniline was the amine used. Chromatography using elution with methylene chloride/methanol/ammonium hydroxide [8:1:0.1] afforded the title compound (61%) as a white solid: mp, 194–195° C.; $R_f$=0.25 in methylene chloride/methanol/ammonium hydroxide [10:1:0.1]; LRMS (m/z, relative intensity) 370 ([$M^+$ with $^{37}Cl$], 14), 369 (9), 368 ([$M^+$ with $^{35}Cl$], 50), 280 (16), 241 (17), 127 (100); HRMS calculated for $C_{20}H_{21}ClN_4O$ with [$^{35}Cl$]368.1406, found 368.1403.

E. 1-(2-(4-Chlorophenylmethylaminocarbonyl)-1H-indol-4-yl)-4-methylpiperazine p-Chlorobenzylamine was the amine used. Chromatography using elution with methylene chloride/methanol/ammonium hydroxide [8:1:0.1] afforded the title compound (86%) as a pale yellow solid: mp, 197–200° C.; $^{13}C$ NMR ($CDCl_3$) δ161.7, 146.6, 137.8, 136.6, 133.5, 129.2, 128.9, 125.5, 121.6, 107.7, 106.6, 101.0, 55.4, 51.1, 46.0, 43.0; LRMS (m/z, relative intensity) 384 ([$M^+$ with $^{37}Cl$], 36), 383 (28), 382 ([$M^+$ with $^{35}Cl$], 100), 367 (13), 312 (20), 241 (23), 220 (32), 147 (39); HRMS calculated for $C_{21}H_{23}ClN_4O$ with [$^{37}Cl$] 384.1533, found 384.1571.

F. 4-Methyl-1-(2-(pyrid-3-ylmethyl)aminocarbonyl-1H-indol-4-yl)piperazine

3-Aminomethylpyridine was the amine used. Chromatography using elution with methylene chloride/methanol/ammonium hydroxide [10:1:0.1] afforded the title compound (30%) as a white solid: mp, 238–240° C.; $^{13}C$ NMR ($CDCl_3$) δ161.6, 149.1, 148.3, 146.3, 137.8, 135.5, 134.6, 129.5, 124.5, 123.3, 120.9, 106.5, 106.3, 102.9, 55.2, 50.8, 45.8, 40.5; LRMS (m/z, relative intensity) 350 (20), 349 ($M^+$, 100), 334 (11), 312 (23), 279 (23), 241 (35), 170 (36), 125 (32), 71 (45), 70 (48); HRMS calculated for $C_{20}H_{23}N_5O$ 349.1905, found 349.1909.

Analytical calculated for $C_{20}H_{23}N_5O.0.25$ water: C, 67.87; H, 6.69; N, 19.79. Found: C, 67.67; H, 6.80; N, 19.72.

G. 4-Methyl-1-(2-(pyrid-2-ylmethyl)aminocarbonyl-1H-indol-4-yl)piperazine

2-Aminomethylpyridine was the amine used. Chromatography using elution with ethyl acetate/methanol/ammonium hydroxide [5:1:0.1] afforded the title compound (45%) as a white solid: $^1H$ NMR ($CDCl_3$) δ9.42 (br s, indole NH), 8.60 (d, J=4.9 Hz, 1H), 7.72–7.67 (m, 1H), 7.59 (br t, amide NH), 7.35 (d, J=7.8 Hz, 1H), 7.25–7.15 (m, 2H), 7.07 (d, J=8.3 Hz, 1H), 6.97 (s, 1H), 6.60 (d, J=7.4 Hz, 1H), 4.79 (d, J=5.1 Hz, 2H), 3.29 (br t, 4H). 2.73 (br t, J=4.5 Hz, 4H), 2.43 (s, 3H); LRMS (m/z, relative intensity) 350 (27), 349 ($M^+$, 100), 319 (5), 279 (20), 241 (21); HRMS calculated for $C_{20}H_{23}N_5O$ 349.1905, found 349.1901.

Analytical calculated for $C_{20}H_{23}N_5O.0.5$ water: C, 67.02; H, 6.75; N, 19.54. Found: C, 67.34; H, 6.75; N, 19.15.

H. 4-Methyl-1-(2-(pyrid-4-ylmethyl)aminocarbonyl-1H-Indol-4-yl)piperazine

4-Aminomethylpyridine was the amine used. Chromatography using elution with methylene chloride/methanol/ammonium hydroxide [15:1:0.1] afforded the title compound (23%) as a pale yellow solid: mp, 230–231° C.; $^{13}C$ NMR ($CD_3OD$) δ164.3, 150.8, 150.2, 147.4, 139.7, 130.4, 126.4, 124.0, 122.6, 108.4, 108.3, 104.0, 56.3, 52.2, 46.6, 43.3; LRMS (m/z, relative intensity) 350 (23), 349 ($M^+$, 100), 334 (9), 306 (14), 279 (21), 170 (23); HRMS calculated for $C_{20}H_{23}N_5O$ 349.1905, found 349.1884.

Analytical calculated for $C_{20}H_{23}N_5O.0.75$ water: C, 66.19; H, 6.80; N, 19.30. Found: C, 66.18; H, 6.61; N, 19.54.

I. 4-Methyl-1-(2-(2-phenylethylaminocarbonyl)-1H-indol-4-yl)piperazine

Phenethylamine was the amine used. Chromatography using elution with methylene chloride/methanol/ammonium hydroxide [15:1:0.1] afforded the title compound (54%) as an off-white solid: mp, 82–83° C.; $^{13}C$ NMR ($CDCl_3$) δ161.6, 146.6, 138.8, 137.6, 129.3, 128.9, 128.7, 126.7, 125.3, 121.4, 107.4, 106.6, 100.6, 55.4, 51.4, 46.2, 40.9, 36.0; LRMS (m/z, relative intensity) 363 (13), 362 ($M^+$, 24), 347 (5), 272 (77), 202 (21), 170 (30), 85 (73), 83 (100); HRMS calculated for $C_{22}H_{26}N_4O$ 362.2109, found 362.2131.

Analytical calculated for $C_{22}H_{26}N_4O.0.25$ water: C, 72.00; H, 7.28; N, 15.27. Found: C, 71.67; H, 7.51; N, 15.65.

J. 1-(2-(Benzhydrylaminocarbonyl)-1H-indol-4-yl)-4-methylpiperazine

Aminodiphenylmethane was the amine used. Chromatography using elution with 4% methanol in methylene chloride afforded the title compound (31%) as a pale yellow powder: mp, 232–234° C.; $^{13}C$ NMR ($CDCl_3$) δ160.9, 146.7, 141.3, 137.9, 128.8, 128.5, 127.7, 126.9, 125.4, 121.5, 107.4, 106.7, 101.1, 57.3, 55.5, 51.4, 46.1; LRMS (m/z, relative intensity) 425 (13), 424 ($M^+$, 38), 362 (100), 347 (9), 292 (16), 272 (82), 257 (29), 241 (27), 167 (45); HRMS calculated for $C_{27}H_{28}N_4O$ 424.2265, found 424.2253.

Analytical calculated for $C_{27}H_{28}N_4O.0.25$ water: C, 75.58; H, 6.70; N, 13.06. Found, C: 75.45; H, 6.77; N, 13.12.

K. 4-Methyl-1-(2-(1R-phenylethylaminocarbonyl)-1H-indol-4-yl)piperazine (R)-(+)-a-Methylbenzylamine was the amine used. Chromatography using elution with methylene chloride/methanol/ammonium hydroxide [15:1:0.1] afforded the title compound (52%) as a pale red solid: mp, 106–108° C.; $^{13}$C NMR (CDCl$_3$) δ161.1, 146.7, 143.1, 137.9, 129.2, 128.8, 127.5, 126.3, 125.2, 121.5, 107.3, 106.8, 100.8, 55.5, 51.5, 49.1, 46.2, 21.9; LRMS (m/z, relative intensity) 362 (M$^+$, 5), 272 (28), 202 (9), 170 (11), 85 (64), 83 (100); HRMS calculated for C$_{22}$H$_{26}$N$_4$O 362.2109, found 362.2113; [α]$^{25}$=−191° (c=1, methanol).

Analytical calculated for C$_{22}$H$_{26}$N$_4$O.0.5 water: C, 71.13; H, 7.33; N, 15.08. Found: C, 71.03; H, 7.60; N, 15.32.

L. 4-Methyl-1-(2-(1S-phenylethylaminocarbonyl)-1H-indol-4-yl)piperazine (S)-(−)-a-Methylbenzylamine was the amine used. Chromatography using elution with methylene chloride/methanol/ammonium hydroxide [15:1:0.1] afforded the title compound (38%) as a pale red solid: mp, 105–107° C.; $^{13}$C NMR (CDCl$_3$) δ161.1, 146.7, 143.0, 137.9, 129.2, 128.8, 127.5, 126.3, 125.2, 121.4, 107.4, 106.7, 100.7, 55.5, 51.5, 49.0, 46.2, 21.8; LRMS (m/z, relative intensity) 362 (M$^+$, 9), 272 (100), 202 (21), 170 (30), 85 (61), 83 (91); HRMS calculated for C$_{22}$H$_{26}$N$_4$O 362.2109, found 362.2120; [α]$^{25}$=+192° (c=1, methanol).

Analytical calculated for C$_{22}$H$_{26}$N$_4$O.water: C, 69.44; H, 7.42; N, 14.73. Found: C, 69.35; H, 7.44; N, 15.11.

M. 4-Methyl-1-(2-(methylaminocarbonyl)-1H-indol-4-yl)piperazine

Methylamine was the amine used. Chromatography using elution with methylene chloride/methanol/ammonium hydroxide [15:1:0.04] afforded the title compound (88%) as a pale yellow solid: mp, 83–85° C.; $^{13}$C NMR (CD$_3$OD) δ164.7, 146.9, 139.5, 131.0, 125.8, 122.6, 108.4, 108.0, 103.0, 56.0, 51.3, 45.3, 26.4; LRMS (m/z, relative intensity) 272 (M$^+$, 14), 202 (4), 170 (4), 68 (100); HRMS calculated for C$_{15}$H$_{20}$N$_4$O 272.1639, found 272.1642.

N. 1-(2-(3,4-Dichlorophenylmethylaminocarbonyl)-1H-indol-4-yl)-4-methylpiperazine 3,4-Dichlorobenzylamine was the amine used. Chromatography using elution with methylene chloride/methanol/ammonium hydroxide [15:1:0.1] afforded the title compound (53%) as a pale yellow solid: mp, 162–164° C.; $^{13}$C NMR (CDCl$_3$) δ161.8, 146.7, 138.5, 137.7, 130.7, 130.4, 129.6, 129.1, 128.7, 127.1, 126.5, 125.6, 107.6, 106.6, 101.4, 55.3, 51.2, 46.0, 45.3, 42.5; LRMS (m/z, relative intensity) 419 (14), 418 ([M$^+$ with $^{37}$Cl], 43), 417 (14), 416 ([M$^+$ with $^{35}$Cl], 76), 349 (25), 212 (32), 174 (61), 159 (100); HRMS calculated for C$_{21}$H$_{22}$Cl$_2$N$_4$O with $^{35}$Cl 416.1174, found 416.1118.

Analytical calculated for C$_{21}$H$_{22}$Cl$_2$N$_4$O.0.1 water: C, 60.18; H, 5.34; N, 13.37. Found: C, 60.04; H, 5.47; N, 13.00.

O. 1-(2-(4-chlorophenylmethoxycarbonyl)-1H-indol-4-yl)-4-methylpiperazine

4-Chlorobenzyl alcohol was the alcohol used. Chromatography using elution with methylene chloride/methanol/ammonium hydroxide [15:1:0.1] afforded the title compound (20%) as a pale green solid: mp, 154–155° C.; $^{13}$C NMR (CDCl$_3$) δ161.6, 147.3, 138.4, 135.0, 134.3, 129.8, 128.9, 126.6, 125.3, 121.3, 108.1, 107.3, 106.1, 65.8, 55.4, 51.3, 46.1; LRMS (m/z, relative intensity) 385 ([M$^+$ with $^{37}$Cl], 30), 384 (18), 383 ([M$^+$ with $^{35}$Cl], 100), 368 (7), 339 (7), 313 (17), 298 (6), 124 (13); HRMS calculated for C$_{21}$H$_{22}$ClN$_3$O$_2$ with $^{35}$Cl 383.1403, found 383.1413.

Analytical calculated for C$_{21}$H$_{22}$ClN$_3$O$_2$.0.75 water: C, 63.47; H, 5.96; N, 10.57. Found: C, 63.50; H, 5.83; N, 10.49.

P. 1-(2-(4-Methoxyphenylmethoxycarbonyl)-1H-indol-4-yl)-4-methylpiperazine

4-Methoxybenzyl alcohol was the alcohol used. Chromatography using elution with methylene chloride/methanol/ammonium hydroxide [20:1:0.1] afforded the title compound (73%) as a white solid: $^{13}$C NMR (CDCl$_3$) δ162.0, 159.9, 147.2, 138.2, 130.3, 128.1, 126.4, 125.6, 121.3, 114.0, 107.9, 107.2, 106.0, 66.5, 55.4, 55.3, 51.3, 46.1; LRMS (m/z,relative intensity) 380 (89), 379 (M$^+$, 95), 364 (30), 309 (32), 214 (32), 171 (41), 121 (100); HRMS calculated for C$_{22}$H$_{25}$N$_3$O$_3$ 379.1898, found 379.1880.

Analytical calculated for C$_{22}$H$_{25}$N$_3$O$_3$.0.25 water: C, 68.82; H, 6.69; N, 10.94. Found: C, 68.93; H, 6.76; N, 10.84.

Q. 1-(2-(4-Methoxyphenylmethylaminocarbonyl)-1H-indol-4-yl)-4-methylpiperazine 4-Methoxybenzyl amine was the aminel used. Chromatography using elution with methylene chloride/methanol/ammonium hydroxide [33: 1:0.1] afforded the title compound (4%) as a white solid: $^{13}$C NMR (CDCl$_3$) δ161.5, 159.2, 146.7, 137.8, 130.1, 129.3, 129.1, 125.3, 114.2, 107.4, 106.6, 101.0, 55.4, 55.3, 51.3, 46.1, 43.2; LRMS (m/z, relative intensity) 378 (M$^+$, 18), 334 (55), 242 (79), 121 (27), 91 (100); HRMS calculated for C$_{22}$H$_{26}$N$_4$O 378.2058, found 378.2120.

R. 1-(2-(4-Fluorophenylmethylaminocarbonyl)-1H-indol-4-yl)-4-methylpiperazine 4-Fluorobenzyl amine was the amine used. Chromatography using elution with methylene chloride/methanol/ammonium hydroxide [15:1:0.1] afforded the title compound (14%) as a white foam: $^{13}$C NMR (acetone-d$_6$) δ162.2, 161.0, 147.9, 138.8, 136.7, 130.3, 130.1, 125.3, 122.2, 115.8, 115.6, 107.1, 102.3, 56.1, 51.9, 46.3, 42.6; LRMS (m/z, relative intensity) 367 (25), 366 (M$^+$, 100), 351 (4), 331 (14), 296 (18), 267 (14), 241 (18), 170 (21), 109 (62); HRMS calculated for C$_{21}$H$_{23}$FN$_4$O 366.1858, found 366.1860.

S. 4Methyl-1-(2-(4-trifluoromethylphenylmethoxycarbonyl)-1H-indol-4-yl)piperazine 4-Trifluoromethylbenzyl amino was the amine used. Chromatography using elution with methylene chloride/methanol/ammonium hydroxide [15:1:0.1] afforded the title Compound (16%) as a pale yellow foam: mp, 52–54° C.; IR (KBr) 3263 (br), 1637, 1620, 1581, 1553, 1513, 1455, 1419 cm$^{-1}$; $^{13}$C NMR (acetone-d$_6$) δ162.3, 147.8, 145.3, 138.9, 130.3, 129.0, 128.8, 126.0, 126.0, 125.7, 125.4, 122.2, 107.2, 102.5, 56.1, 51.9, 46.3, 42.9; FAB LRMS (m/z, relative intensity) 418 (32), 417 (MH$^+$, 100), 259 (22), 176 (65).

T. 1-(2(4-Bromophenylmethylaminocarbonyl)-1H-indol-4-yl)-4-methylpiperazine

4-Bromobenzyl amine was the amine used. Chromatography using elution with methylene chloride/methanol/ ammonium hydroxide [15:1:0.1] afforded the title compound (14%) as a white solid: $^{13}$C NMR (acetone-$d_6$) δ162.3, 147.8, 140.0, 138.9, 132.1, 130.4, 125.3, 122.3, 121.0, 107.2, 107.1, 102.4, 56.1, 51.9, 46.3, 42.8; LRMS (m/z, relative intensity) 429 (34), 428 ([M$^+$ with $^{51}$Br], 89), 427 (36), 426 ([M$^+$ with $^{79}$Br], 100), 413 (10), 411 (11), 241 (32), 71 (45), 70 (39); HRMS calculated for $C_{21}H_{23}BrN_4O$ 426.1057, found 426.1033.

U. 1-(2-(4-Aminosulfonylphenylmethylaminocarbonyl)-1H-indol-4-yl)-4-methylpiperazine 4-(Aminomethyl)benzenesulfonamide was the amine used. Chromatography using elution with methylene chloride/methanol/ammonium hydroxide [4:1:0.1] afforded the title compound (62%) as a white solid: mp, 130–131° C.; IR (KBr) 3329 (br), 1639, 1604, 1580, 1551, 1510, 1457, 1429, 1411 cm$^{-1}$; FAB LRMS (m/z, relative intensity) 429 (28), 428 (MH$^+$, 100), 309 (41); FAB HRMS calculated for $C_{21}H_{25}N_5O_3S.H^+$ [with $^{32}$S] 428.1759, found 428.1752.

V. 1-(2-(4-Butoxyphenylmethoxycarbonyl)-1H-indol-4-yl)-4-methylpiperazine

4-Butoxybenzyl alcohol was used. Chromatography using elution with methylene chloride/methanol/ammonium hydroxide [15:1:0.1] afforded the title compound (16%) as a white solid: IR (KBr) 3329 (br), 1705 (br), 1611, 1581, 1514, 1455, 1435, 1412 cm$^{-1}$; $^{13}$C NMR (acetone-$d_6$) δ162.0, 160.1, 148.1, 139.9, 130.9, 129.0, 128.8, 126.6, 121.9, 115.2, 107.8, 107.4, 107.1, 68.1, 66.5, 56.1, 52.0, 46.3, 31.9, 19.8, 14.0; FAB LRMS (m/z, relative intensity) 423 (35), 422 (MH$^+$, 100).

W. 4-Methyl-1-(2-(4-biphenylmethoxycarbonyl)-1H-indol-4-yl)piperazine

4-Biphenylbenzyl alcohol was the alcohol used. Chromatography using elution with methylene chloride/methanol/ammonium hydroxide [15:1:0.1] afforded the title compound (40%) as a white solid: mp, 123–124° C.; $^{13}$C NMR (acetone-$d_6$) δ162.0, 148.2, 141.6, 141.2, 139.9, 136.4, 129.6, 129.6, 128.2, 127.8, 127.6, 126.7, 121.9, 108.1, 107.4, 107.1, 66.4, 56.0, 52.0, 46.3; LRMS (m/z, relative intensity) 426 (36), 425 (M$^+$, 100), 410 (5), 355 (10), 270 (75), 253 (43); HRMS calculated for $C_{27}H_{27}N_3O_2$ 425.2105, found 425.2062.

Analytical calculated for $C_{27}H_{27}N_3O_2.1.1$ water: C, 72.82; H, 6.61; N, 9.44. Found: 72.52; H, 6.23; N, 9.12.

X. 4-Methyl-1-(2-(4-(4-phenylmethoxy)phenylmethoxycarbonyl)-1H-indol-4-yl)piperazine 4-Benzyloxybenzyl alcohol was the alcohol used. Chromatography using elution with methylene chloride/methanol/ammonium hydroxide [15:1:0.1] afforded the title compound (20%) as a pale yellow solid: mp, 68–69° C.; $^{13}$C NMR (acetone-$d_6$) δ162.0, 159.7, 148.1, 139.8, 138.2, 130.9, 129.5, 129.2, 128.5, 128.3, 126.6, 121.9, 115.6, 107.9, 107.4, 107.1, 70.3, 66.5, 56.1, 52.0, 46.3; LRMS (m/z, relative intensity) 456 (9), 455 (M$^+$, 32), 300 (10), 257 (13), 197 (20), 91 (100); HRMS calculated for $C_{28}H_{29}N_3O_3$ 455.2211, found 455.2214.

Analytical calculated for $C_{28}H_{29}N_3O_3.0.5$ water: C, 72.39;, H, 6.51; N, 9.05. Found: C, 72.03; H, 6.47; N, 9.06.

Y. 1-(2-(4-Ethoxyphenylmethoxycarbonyl)-1H-indol-4-yl)-4-methylpiperazine

4-Ethoxybenzyl alcohol was the alcohol used. Chromatography using elution with methylene chloride/methanol/ammonium hydroxide [15:1:0.1] afforded the title compound (18%) as an off-white foam: $^{13}$C NMR (acetone-$d_6$) δ162.0, 159.9, 148.1, 139.8, 130.9, 129.1, 126.7, 126.6, 121.9, 115.1, 107.9, 107.4, 107.1, 66.5, 63.9, 56.1, 52.0, 46.3, 15.0; LRMS (m/z, relative intensity) 394 (14), 393 (45), 378 (4), 361 (5), 341 (11), 201 (16) 135 (100); HRMS calculated for $C_{23}H_{27}N_3O_3$ 393.2054, found 393.1982.

Analytical calculated for $C_{23}H_{27}N_3O_3.0.5$ water: C, 68.64; H, 7.01; N, 10.44. Found: C, 68.38: H, 7.02; H, 10.43.

Z. 1-(2-(4-Chlorophenylmethylaminocarbonyl)-1-methyl-1H-indol-4-yl)-4-methylpiperazine 4-Chlorobenzyl amine was the amine used. Chromatography using elution with methylene chloride/methanol/ammonium hydroxide [20:1:0.1] afforded the title compound (62%) as a yellow solid: mp, 147–150° C.; $^{13}$C NMR (CD$_3$OD) δ165.0, 147.6, 142.0, 139.2, 133.9, 131.4, 130.2, 129.6, 126.1, 121.2, 108.3, 106.0, 105.0, 56.3, 52.2, 46.2, 43.4, 32.1; LRMS (m/z, relative intensity) 398 ([M$^+$ with $^{37}$Cl], 34), 397 (25), 396 ([M$^+$ with $^{35}$Cl], 100), 381 (11), 273 (57), 125 (50), 71 (55); HRMS calculated for $C_{22}H_{25}ClN_4O$ 396.1720, found 396.1719.

EXAMPLE 3

3-(4-Chlorophenylmethyl)-5-(4-(4-methylpiperazin-1-yl)-1H-indol-2-yl)-1,2,4-oxadiazole A solution of carbonyl diimidazole (0.95 g, 5.86 mmol, 2.1 equivalents) and 4-(4-Methylpiperazin-1 yl)indole-2-carboxylic acid (0.710 g, 2.74 mmol) in anhydrous tetrahydrofuran (5 mL) was heated at 50° C. under nitrogen for 5 hours. The reaction was cooled to room temperature, and a preformed solution of 4-fluorophenol (2.90 g, 25.9 mmol, 9.4 equivalents) and sodium hydride (60% in oil, 1.17 g, 29.2 mmol, 10,7 equivalents) in anhydrous tetrahydrofuran (15 mL) was added rapidly. The resulting reaction solution was stirred at room temperature under nitrogen for 12 hours. Ethyl acetate (50 mL) was added to the reaction solution, and the resulting solution was extracted with a saturated solution of sodium hydrogen carbonate (2×25 mL). The organic layer was dried (magnesium sulfate), and evaporated under reduced pressure. The residue was chromatographed using silica gel (approximately 100 g) and elution with 20% methanol in ethyl acetate to afford crude 4-methyl-1-(2-(4-fluorophenoxycarbonyl)-1H-indol-4-yl)piperazine (0.225 g, 0.68 mmol crude, 25% crude).

Hydroxylamine hydrochloride (3.47 g, 50 mmol, 2.5 equivalents) was added to a stirred solution of sodium (1.2 g, 52 mmol, 2.6 equivalents) was dissolved in absolute methanol (25 mL), and the resulting reaction mixture was stirred at 0° C. under nitrogen for 30 minutes. Then a solution of 4-chlorobenzonitrile (3.02 g, 20 mmol) in absolute methanol (17 mL) was added, and the resulting reaction mixture was stirred at reflux for 16 hours. The reaction mixture was then cooled, filtered, and the filtrate was evaporated under reduced pressure to afford crude (4-chlorophenyl)acetamidoxime (4.34 g, assumed 100%).

To a stirred solution of (4-chlorophenyl)acetamidoxime (2.21 g from above, assumed 10 mmol, 15 equivalents) and sodium hydride (60% in oil, 0.460 g, 11.5 mmol, 17 equivalents) in anhydrous tetrahydrofuran (25 mL) was added crude 4-methyl-1-(2-(4-fluorophenoxycarbonyl)-1H-indol4-yl)piperazine (0.225 g from above, assumed 0.68 mmol), and the resulting reaction mixture was heated at reflux under nitrogen for 6 hours. A saturated solution of sodium hydrogen carbonate (25 mL) was added, and the resulting aqueous mixture was extracted with ethyl acetate (2×25 mL). The organic extracts were combined, dried (magnesium sulfate), and evaporated under reduced pressure. The residue was chromatographed using silica gel (approximately 25 g) and elution with methylene chloride/methanol/ammonium hydroxide [10:1:0.1] to afford the title compound (0.013 g, 0.03 mmol, 4%) as an off-white foam: $^{13}$C NMR (acetone-$d_6$) δ170.3, 169.5, 147.2, 139.7, 135.0, 132.3, 130.7, 128.5, 126.2, 121.5, 119.9, 107.0, 106.4, 106.2, 55.3, 51.2, 45.5, 31.0; LRMS (m/z, relative intensity) 409 ([M$^+$ with $^{37}$Cl], 30), 408 (27), 407 ([M$^+$ with $^{35}$Cl], 100), 392 (7), 337 (23), 322 (16), 170 (16), 70 (41); HRMS calculated for $C_{22}H_{22}ClN_5O$ [with $^{35}$Cl] 407.1516, found 407.1516.

EXAMPLE 4

1-(2-Methyl-1H-indol-4-yl)piperazine

A solution of 4-methyl-1-(2-methyl-1H-indol-4-yl)piperazine (0.510 g, 2.22 mmol) and 2,2,2-trichloroethyl chloroformate (5 mL) was heated at 100–110° C. for 48 hours. The reaction solution was cooled, and methylene chloride (200 mL) followed carefully by a saturated solution of sodium hydrogen carbonate (20 mL) were added. The organic layer was removed, dried (potassium carbonate), and evaporated under reduced pressure. The residue was chromatographed using silica gel (approximately 300 g) using elution with 10% ethyl acetate in hexanes to afford 4-(2,2,2-trichloroethoxycarbonyl)-1-(2-methyl-1H-indol-4-yl)piperazine as a white amorphous solid (0.74 g, 1.89 mmol, 85%): FAB LRMS (m/z, relative intensity) 394 (9), 392 (27), 390 ([MH$^+$ with $^{35}$Cl], 32), 358 (18), 356 (29), 216 (99), 194 (100). This compound was used directly as outlined below.

A mixture of 4-(2,2,2-trichloroethoxycarbonyl)-1-(2-methyl-1H-indol-4-yl)piperazine (0.70 g, 1.79 mmol, used directly from above), zinc dust (2.0 g), tetrahydrofuran (15 mL), and a solution of $KH_2PO_4$ (1.0 M, 3 mL) was vigorously stirred at room temperature under nitrogen for 6 hours. The resulting reaction mixture was filtered, and the filtrate was evaporated under reduced pressure. The residue was chromatographed using silica gel (approximately 75 g) and elution with methylene chloride/methanol/ammonium hydroxide [6:1:0.1] to afford the title compound (0.170 g, 0.79 mmol, 44%) as an off-white amorphous solid: $R_f$=0.2 in methylene chloride/methanol/ammonium hydroxide [6:1:0.1]; $^1$H NMR (CD$_3$OD) δ7.02 (d, J=8.0 Hz, 1H), 6.94 (t, J=7.7 Hz, 1H), 6.54 (dd, J=1.0 and 7.3 Hz, 1H), 6.15 (s, 1H), 4.89 (s, exchangeable protons), 3.43 (br t, 4H), 3.40 (br t, 4H), 2.41 (s, 3H).

EXAMPLE 5

1-(3-Formyl-2-methyl-1H-indol-4-yl)-4-methylpiperazine

To a stirred solution of 4-methyl-1-(2-methyl-1H-indol-4-yl)piperazine (0.247 g, 1.08 mmol) in anhydrous N,N-dimethylformamide (1 mL) at 0° C. was added dropwise a solution of phorsphorus oxychloride (0.16 g, 1.04 mmol) in anhydrous N,N-dimethylformamide (1 mL). The resulting reaction solution was stirred at room temperature under nitrogen for 2 hours. An aqueous solution of sodium hydroxide (10% by weight, 3 mL) was then added, and the resulting solution was stirred at room temperature under nitrogen overnight. The reaction solution was then evaporated under reduced pressure, and the residue was chromatographed using silica gel (approximately 50 g) and elution with methylene chloride/methanol/ammonium hydroxide [10:1:0.1] to afford the title compound (0.060 g, 0.23 mmol, 22%) as an off-white foam: $^1$H NMR (DMSO-$d_6$) δ12.14 (br s, NH), 10.46 (s, 1H), 7.14–7.08 (m, 2H), 6.88 (dd, J=1.4 and 7.1 Hz, 1H), 3.11 (br m, 8H), 2.66 (s, 3H); FAB LRMS (m/z, relative intensity) 259 (16), 258 (MH$^+$, 100).

EXAMPLE 6

4-(4-Methylpiperazin-1yl)indole-2-carboxylic acid

A solution of 1-(2-(ethoxycarbonyl)-1H-indol-4-yl)-4-methylpiperazine (0.91 g, 3.17 mmol), lithium hydroxide hydrate (0.136 g, 3.17 mmol, 1.0 equivalent), tetrahydrofuran (20 mL), and water (4 mL) was heated at reflux under nitrogen for 16 hours. The resulting reaction mixture was evaporated under reduced pressure, and the residue was chromatographed using silica gel (approximately 30 g) and elution with methylene chloride/methanol/ammonium hydroxide [3:2:0.2] to afford the title compound (0.40 g, 1.54 mmol, 49%) as a white solid: mp, 272–273° C.; R$_f$ =0.05 in methylene chloride/methanol/ammonium hydroxide [5:1:0.1]; $^{13}$C NMR (D$_2$O) δ169.4, 145.0, 137.5, 132.9, 124.7, 120.7, 108.2, 107.3, 103.7, 58.7, 53.7, 51.0; LRMS (m/z, relative intensity) 260 (18), 259 (M$^+$, 100), 244 (9), 215 (7), 170 (24); HRMS calculated for $C_{14}H_{17}N_3O_2$ 259.1322, found 259.1325.

EXAMPLE 7

1-Methyl-4-(4-methylpiperazin-1yl)indole-2-carboxylic acid

A solution of 1-(2-(ethoxycarbonyl)-1-methylindol-4-yl)-4-methylpiperazine (0.117 g, 0.39 mmol), lithium hydroxide hydrate (0.035 g, 0.83 mmol, 2 equivalents) in tetrahydrofuran (2 mL) and water (0.5 mL) was heated at reflux under nitrogen for 16 hours. The resulting reaction solution was evaporated under reduced pressure, and the residue was directly chromatographed using silica gel (approximately 10 g) and elution with methylene chloride/methanol/ammonium hydroxide [5:1:0.1] afforded the title compound (0.097 g, 0.34 mmol, 91%) as a yellow solid: $^1$H NMR (CD$_3$OD) δ7.20–7.12 (m, 2H), 7.08 (s, 1H), 6.58 (dd, J=1.1 and 7.1 Hz, 1H), 4.90 (s, exchangeable H), 4.03 (s, 3H), 3.38 (br t, 4H), 3.34 (s, 3H), 3.28 (br t, 4H); LRMS (m/z, relative intensity) 274 (18), 273 (M$^+$, 100), 258 (11), 229 (11), 203 (39), 202 (46), 71 (32), 70 (23); HRMS calculated for $C_{15}H_{19}N_3O_2$ 273.1479, found 273.1479.

EXAMPLE 8

Ethyl 1-methyl-4-nitroindole-2-carboxylate

To a stirred solution of ethyl 4-nitroindole-2-carboxylate (1.57 g, 6.70 mmol) in anhydrous tetrahydrofuran (20 mL) at 0° C. under nitrogen was added sodium hydride (60% in oil, 0.375 g, 9.4 mmol, 1.4 equivalents), and the resulting effervescing mixture was stirred at room temperature under nitrogen for 30 minutes. Then, methyl iodide (1.71 g, 12.0 mmol, 1.8 equivalents) was added dropwise, and the resulting reaction solution was stirred at room temperature under nitrogen for 48 hours. A saturated solution of sodium hydrogen carbonate was then added, and the resulting aqueous mixture was extracted with ethyl acetate (2×30 mL). The organic extracts were combined, dried (sodium sulfate), and evaporated under reduced pressure. The residue was chromatographed using silica gel (approximately 50 g) and elution with 20% ethyl acetate in hexanes to afford the title compound (0.35 g, 1.41 mmol, 21%) as a yellow solid: $R_f$=0.30 in 20% ethyl acetate in hexanes; $^1$H NMR (acetone-$d_6$) δ8.18 (d, J=7.9 Hz, 1H), 8.08 (d, J=8.1 Hz, 1H), 7.78 (s, 1H), 7.57 (t, J=8.1 Hz, 1H), 4.43 (q, J=7.1 Hz, 2H), 4.21 (s, 3H), 1.42 (t, J=7.1 Hz, 3H).

EXAMPLE 9

4-(1-Methyl-piperidin-4-yl)-1H-indole-2-carboxylic acid 4-chlorobenzylamide 4-(1-Methyl-4hydroxy-piperidin-4-yl)-1H-indole To a cold (−78° C.) solution of 4-bromoindole (1.9 g) in anhydrous tetrahydrofuran (50 ml) was added 1.7 M t-butyllithium (20 ml). The reaction was stirred 10 min. at −78° C., at which point the cold bath was removed and the reaction was allowed to warm for 10 min. The cold bath was then replaced and a solution of 1-methyl-4-piperidone (1.47 g) in anhydrous tetrahydrofuran (10 ml, followed by a 5 ml rinse), was slowly added to the reaction. The reaction was stirred for 30 min. and then warmed to room temperature and quenched with saturated sodium bicarbonate (1 ml) and brine (20 ml). The resulting mixture was extracted with ethyl acetate (3×125 ml). The combined organic portions were dried over potassium carbonate, filtered and then concentrated to yield 4.3 g of a green waxy solid. This material was granulated with 20 ml methylene chloride and filtered to yield a light green solid 0.831 g (36%).

4-(1-methyl-3,4-dihydro-piperidin-4-yl)-1H-indole

To a stirred suspension of the product from the above step in anhydrous dioxane (15 ml) was added para-toluenesulfonic acid (0.72 g). The reaction was brought to a reflux and stirred for 3 hours. The reaction was then concentrated under reduced pressure and adhered to silica gel (2 grams). This powder was then placed on top of a pad of approximately 100 g of silica gel and eluted (25-10:1:0.1 methylene chloride/methanol/0.1 ammonium hydroxide) to yield the title compound as a tan foam (400 mg).

4-(1-methyl-piperidin-4-yl)-1H-indole

The product was from the above step (383 mg, a solution of above solvents) was dissolved into a methanol (5 ml) and acetic acid (2 ml) mixture. The resulting solution was carefully poured onto 0.91 g Pearleman's catalyst (Pd(OH)$_2$/C) in a Parr hydrogenation bottle (250 ml). The bottle was filled and purged with nitrogen gas, and then refilled with hydrogen gas, pressurized to 50 psi with hydrogen gas, and shaken for 2 hours. The reaction mixture was diluted with methanol and methylene chloride, filtered and the filtrates concentrated to yield a brown oil. This material was taken up in methylene chloride and dried over potassium carbonate (5 g), filtered and concentrated to yield the title compound as a tan foam (368 mg, 96%).

4-(1-Methyl-piperidin-4-yl)-1-(benzenesulfonyl)-indole

To a stirring solution of the product from the above step in anhydrous tetrahydrofuran (5 ml) was added sodium hydride (333 mg, 60% dispersion in oil). The reaction was stirred 40 minutes, at which time benzenesulfonyl chloride (1.3 g) was added and the reaction stirred an additional 30 minutes. The reaction was then diluted with ethyl acetate and quenched with saturated sodium bicarbonate solution (1 ml). The mixture was filtered and the solids washed with ethyl acetate and 10% methanol/ethyl acetate. The combined filtrates were concentrated under reduced pressure to yield a red oil. This material was vacuum filtered through approximately 60 g silica gel (wet with methylene chloride and eluted with 30-15:1:.01 methylene chloride/methanol/ammonium hydroxide) to yield the title compound (251 mg).

4-(1-Methyl-piperidin-4-yl)-1-(benzenesulfonyl)-indole-2-carboxyl-benzylate

To a cold (−78° C.) stirring solution of the compound from the previous step (219 mg) in anhydrous tetrahydrofuran (5 ml) was added 0.42 ml of t-butyllithium (1.7 M in pentanes). After 10 min. the cold bath was removed and the reaction stirred for 30 min at reduced temperature (temperature less than 0° C.). The cold bath was then replaced and the reaction was stirred an additional 10 min. Benzyl chloroformate (0.10 ml) was then added and the reaction was stirred for 45 minutes at 0° C. A volume of water (0.2 ml) was added to the reaction and the resulting mixture was stirred for 10 minutes at which point the cold bath was removed and the reaction was allowed to warm to room temperature. The reaction was then diluted (with 50:1 ethyl acetate/methanol) and adhered to approximately 1 gram of silica gel. The mixture was flash chromatographed (from 25 g silica gel) and eluted (30-15:1:0.1 methylene chloride/methanol/ammonium hydroxide) to yield the title compound as a green oil, (224 mg/74%).

4-(1-Methyl-piperidin-4-yl)-1-(benzenesulfonyl)-indole-2-carboxylic acid

To a stirring solution of the product from the previous step (183 mg) in anhydrous tetrahydrofuran (4.5 ml) was added water (0.5 ml) and lithium hydroxide (63 mg). The reaction was heated to reflux, and stirred for 5 hours. The reaction was cooled and adhered to silica gel (0.5 g). The powder was vacuum filtered through about 10 gram of silica gel slurried (wet) with methylene chloride and eluted (15-5:1:0.1 methylene chloride/1 methanol/ammonium hydroxide) to yield the title compound as a white powder (128 mg).

4-(1-Methyl-piperidin-4-yl)-1-(benzenesulfonyl)-indole-2-carboxylic acid 4-chlorobenzylamide To a stirring suspension of the product from the previous step in anhydrous tetrahydrofuran (5 ml) was added carbonyl diimidazole (219 mg). The reaction was then stirred for 20 minutes at room temperature and then heated in an 80° C. oil bath for 2 hours. The oil bath was then removed and the reaction stirred for 30 minutes. 4-Chlorobenzylamine (125 μL) was then added to the reaction. The oil bath was replaced and the reaction stirred for 30 minutes at 80° C. The suspension was filtered and the filtrate adhered to silica gel. The resulting powder was flash chromatographed (from 20 g silica gel slurried in methylene chloride and eluted (50-10:1:0.1 methylene chloride/methanol/ammonium hydroxide) to yield the title compound (44 mg).

4-(1-Methyl-piperdin-4-yl)-1H-indole-2-carboxylic acid 4-chlorobenzylamide

To a stirring solution of the product from the prevous step in an isopropyl alcohol (4.5 ml) water (0.5 ml) mixture was added a single (90 mg) pellet of sodium hydroxide. The reaction was brought to reflux and stirred overnight. The following day the reaction was cooled, diluted with methanol and adhered to silica gel. The resulting powder was flash chromatographed (10:1:0.1 ethyl acetate/methanol/triethylamine) to yield the title compound as a white foam (19 mg; 59%; PB-MS showed (M+1)+at 382, which corresponds to the title compound).

EXAMPLE 10

General Synthesis of 4-Nitroindole via Fischer Indolization of 3-nitrophenylhydrazine Derivatives A mixture of 3-nitrophenylhydrazine hydrochloride (1.90 g, 10.0 mmol) and the appropriate ketone (12.5 mmol, 1.25 equivalents) in absolute ethanol (20 mL) was heated at reflux under nitrogen overnight. The resulting reaction solution was evaoprated under reduced pressure, and the residue (assumed hydrazone) was used directly. To this residue was added polyphosporic acid (PPA, 15 g), and the resulting viscous mixture was heated at 100° C. for 1 hour. The resulting black reaction solution was cooled, and ice (50 g) was added carefully with stirring. The resulting aqueous mixture was extracted with methylene chloride (3×50 mL), and these extracts were dried (magnesium sulfate) and evaporated under reduced pressure. If necessary, chromatography of the residue using silica gel (approximately 100 g) and elution with an appropraie solvent system afforded the title compound.

Using the above procedure, the following compounds were prepared:

A. 4-Nitro-2-(pyrid-3-yl)-1H-indole

3-Acetylpyridine was used, and the aqueous extraction was done at pH 10. Recrystallization of the extraction residue using methanol afforded the title compound (11%) as an orange solid: $R_f$=0.35 in 5% methanol in methylene chloride; $^1$H NMR (DMSO-$d_6$) $\delta$12.58 (br s, NH), 9.21 (d, J=0.6 Hz, 1H), 8.61 (dd, J=1.5 and 4.8 Hz, 1H), 8.39–8.34 (m, 1H), 8.08 (dd, J=0.7 and 8.0 Hz, 1H), 7.91 (dd, J=0.7 and 8.0 Hz, 1H), 7.63 (d, J=0.5 Hz, 1H), 7.58–7.53 (m, 1H), 7.35 (t, J=8.0 Hz, 1H); FAB LRMS (m/z, relative intensity) 241 (18), 240 (MH+, 100), 210 (95).

B. 2-(3-canophenyl)-4-nitro-1H-indole

3-Aecetylbenzonitrile was used. Evaporation of the extraction residue afforded the tile compound (11%) as an amorphous yellow solid.

C. 5-Nitro-1-oxo-1,2,3,4-tetrahydro-9H-pyrido[3,4-b]indole

2-Ketopyrid-2-one [C. Herdis and G. Bissinger, Z. Naturforsch. 42b, 785–790 (1987)] was used. Chromatography using elution with 40% ethyl acetate in methylene chloride afforded the true compound (13%) as an amorphous yellow solid: $^1$H NMR (DMSO-$d_6$) $\delta$12.5 (br s, indole NH), 7.95 (d, J=7.8 Hz, 1H), 7.93–7.89 (br m, amide NH) 7.83 (d, J=8.2 Hz, 1H), 7.39 (t, J=8.0 Hz, 1H), 3.52–3.46 (m, 2H), 3.12 (t, J=6.9 Hz, 2H); $^{13}$C NMR (DMSO-$d_6$) $\delta$161.0, 142.3, 139.0, 135.3, 131.4, 122.7, 119.9, 117.9, 115.9, 40.9, 23.0.

D. 2-Methyl-4-nitro-1H-indole

Acetone was used. Chromatography using elution with ethyl acetate/methylene chloride [1:1] afforded the title compound (6%) as an amorphous yellow solid: $R_f$=0.25 in ethyl acetate/hexanes [1:2] $^1$H NMR (DMSO-$d_6$) $\delta$12.5 (br s, indole NH), 7.98 (d, J=8.1 Hz, 1H), 7.74 (dd, J=0.6 and 7.9 Hz, 1H), 7.20 (t, J=7.9 Hz, 1H), 6.80 (br s, 1H), 3.34 (s, 3H).

EXAMPLE 11

4(1-Benzyl-pyrrolidin-3-yl)-2-(3-pyridin-3-yl-methyl-[1,2,4]oxadiazol-5-yl)-1H-indole 1-(benzyl)-4-hydroxy-4-(4-indole)-pyrrolidine To a cold (−78° C.) stirring solution of 4-bromoindole (6.99 g) in anhydrous tetrahydrofuran (70 ml) was added 70 ml of tert-butyllithium, slowly. The reaction was stirred at −78° C. for 10 minutes. The cold bath was then removed and the reaction was slowly warmed to −20° C. The cold bath was then replaced and the reaction was allowed to stir for an additional 10 minutes. 1-Benzyl-3-pyrrolidinone (6.85 g) was then added dropwise, via canula over a 1 hour period as a solution in anhydrous tetrahydrofuran. The reaction was then stirred for 30 minutes at which time the cold bath was removed and the reaction was allowed to warm to −10° C. The reaction was then quenched with saturated sodium bicarbonate (2 ml) and diluted to 400 ml with ethyl acetate. This suspension was filtered and rinsed with ethyl acetate. The filtrates were concentrated, and the resulting solids were dissolved in a water (100 ml), methanol (15ml) and methylene chloride (90 ml) mixture. The resulting biphasic solution was extracted with ethyl acetate and methyleme chloride. The combined organics were dried over sodium sulfate and then filtered and concentrated. The residue was chromatographed (from approximately 265 g of silica gel, and eluted with 33-10:1:0.1 methylene chloride/methanol/ammonium hydroxide) to yield the title compound as a green-brown solid (7.107 g).

1-(benzyl)-4-(4-indole)-3,4-dihydropyrrolidine

To a stirring solution of the compound from the previous step (7.10 g) in anhydrous dioxane was added p-toluenesulfonic acid (4.71 g). The reaction was brought to reflux and was stirred for 15 minutes at which time the oil bath removed. The reaction was then concentrated under reduced pressure and the title compound was used in the next step without further purification.

1-benzyl-4-(4-indole)-pyrrolidine

A solution containing (11.4 g) of the compound from the previous step in 30 ml methanol was carefully poured onto Pearleman's catalyst (7.0 g) in a Parr hydrogenation shaker bottle. The bottle was placed under 50 psi hydrogen gas atmosphere and was shaken for 3 hours. The reaction was then diluted with methylene chloride, filtered through Celite and the catalyst washed with methanol, methylene chloride and methanol/methylene chloride rinses. The combined filtrates were concentrated and the residue was flash chromatographed (300 g silica gel and eluted with 50-17:1:0.1 methylene chloride/methanol/ammonium hydroxide) to yield the title compound as a white solid (1.63 g ).

1-(benzyl)-4-(1-benzenesulfonyl-4yl-indole)-pyrrolidine

To a cold (−78° C.) stirring solution of the compound from the above step in anhydrous tetrahydrofuran (25 ml) was added tert-butyllithium (4.33 ml, 1.7M in pentanes). The cold bath was removed after 10 minutes and the reaction was allowed to warm with stirring for an additional 30 minutes. The cold bath was then replaced and the reaction was stirred for an additional 10 minutes. Benzenesulfonyl chloride (1.1 g, 0.80 ml) was then added to the reaction, via syringe, and the reaction was stirred for 1 hour at −78° C. The cold bath was then removed and the reaction was stirred for 1 hour. The reaction was quenched with saturated sodium bicarbonate (2 ml) and then diluted with ethyl acetate (100 ml) and brine (20 ml). The organic layer was separated, dried over modicum sulfate, filtered and concentrated to yield 2.10 g brown oil. This material was quick-filtered through silica gel (50 g and eluted with a gradient of 1 L of 100:1.0.1, and 1 L 50:1:0.1) to yield the title compound as a white solid (1.171 g).

4-(1-benzyl-pyrrolidin-3-yl)-2-[benzyl-formate]-1-(benzenesulfonyl)-indole

To a cold (−78° C.) stirring solution of the product from the above step in anhydrous tetrahydrofuran (10 ml) was added tert-butyllithium (2.15 ml; dropwise, via syringe). The reaction was then stirred at −78° C. for ten minutes. The cold bath was then removed and the reaction allowed to warm to about 0° C. (30 minutes). The cold bath was replaced and the reaction stirred 10 minutes. Benzyl chloroformate (0.45 ml) was then slowly added to the reaction, via syringe. The reaction was stirred for an additional 10 min, the cold bath removed, and the reaction stirred for 1 hour. The reaction was then quenched with saturated sodium bicarbonate (2 ml) and diluted with ethyl acetate. The organic phase was then washed with brine (2×10 ml). The organic phase was concentrated under reduced pressure to yield crude material (2.0 g). This material was flash chromatographed (from 100 g silica gel, and eluted with a gradient of 100:1:0.1 to 50:1:0.1 methylene chloride/methanol/ammonium hydroxide) to yield the title compound (966 mg).

4-(1-Benzyl-pyrrolidin-3-yl-2-(3-pyridine-3-yl-methyl-[1,2,4]oxadiazol-5-yl)-1H-indole Hydroxylamine hydrochloride (0.188 grams) was added to a solution of sodium spheres (65 mg) dissolved in methanol (50 ml). The reaction was stirred for ten minutes at which time 3-pyridylacetonitrile (128 mg) was added, and the reaction was stirred for an additional 2 hours. The reaction was then filtered and the solution was concentrated under reduced pressure. The resulting residue was suspended in tetrahydrofuran (10 ml) and sodium hydride (48 mg) was added. The resulting suspension was refluxed for 30 minutes. The oil bath was then removed and the reaction was cooled to room temperature. An anhydrous tetrahydrofuran solution containing 0.300 g the compound from the previous step was then added. The oil bath was replaced and the reaction was refluxed for 40 minutes. The reaction was then cooled and diluted with ethyl acetate (30 ml) and slowly quenched with saturated sodium bicarbonate (30 ml). The layers were separated and the aqueous layer extracted with ethyl acetate (100 ml). The combined organics were dried over magnesium sulfate, filtered and then concentrated to yield a yellow oil. This material was flash chromatographed (from 40 g silica gel and eluted with 10% hexane/ethyl acetate) to yield the title compound (38 mg).

What is claimed is:

1. A compound of formula

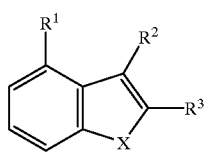

I

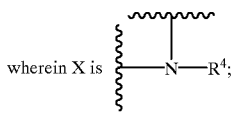

wherein X is —N—R$^4$;

R$^1$ is a group of the formula

II

R$^2$ is hydrogen and R$^3$ is selected from, $(C_1$ to $C_6)$alkyl; —$(C_1$ to $C_3)$alkylaryl, —$(C_1$ to $C_3)$alkylheteroaryl —NH(C=O)R$^6$, —(C=O)NHR$^6$, —O(C=O)R$^6$, —(C=O)OR$^6$, —(C=O)R$^6$, OR$^6$, —SO$_n$R$^6$, —NHSO$_n$R$^6$, —SO$_n$NHR$^6$, aryl, and heteroaryl;

R$^4$ is hydrogen;

R$^5$ is hydrogen or —CH$_3$;

R$^6$ is hydrogen, $(C_1$ to $C_6)$alkyl, —$(C_1$ to $C_3)$alkylaryl, —$(C_1$ to $C_3)$alkylheteroaryl, aryl, heteroaryl, and —(CH$_2$)—Y—R$^7$;

R$^7$ is hydrogen, $(C_1$ to $C_6)$alkyl, —$(C_1$ to $C_3)$alkylaryl, —$(C_1$ to $C_3)$alkylheteroaryl, —(C=O)NHR$^8$, —(C=O)OR$^8$, —(C=O)R$^8$, —OR$^8$, —SO$_n$R$^8$, —SO$_n$NHR$^8$, aryl, and heteroaryl;

R$^8$ is hydrogen, $(C_1$ to $C_3)$alkyl, aryl, heteroaryl, —$(C_1$ to $C_3)$alkylaryl and —$(C_1$ to $C_3)$alkylheteroaryl;

Y is oxygen, —SO$_n$—, or NH;

n is 0, 1, or 2;

and said heteroaryl groups and the heteroaryl moieties of said alkylheteroaryl groups are selected from pyridyl and indolyl;

and said heteroaryl groups and the heteroaryl moieties of said alkylheteroaryl groups may optionally be substituted with from one to three substituents independently selected from $(C_1$ to $C_4)$alkyl, halogen, hydroxy, cyano, carboxamido, nitro, $(C_1$ to $C_4)$alkoxy, —$(C_1$ to $C_3)$alkylaryl, —$(C_1$ to $C_3)$alkylheteroaryl, aryl, heteroaryl, and —(CH$_2$)—Y—R$^7$;

and said aryl groups and the aryl moieties of said alkylaryl groups are phenyl and may optionally be substituted with one to three substituents independently selected from $(C_1$ to $C_4)$alkyl, halogen, hydroxy, cyano, carboxamido, nitro, and $(C_1$ to $C_4)$alkoxy;

provided that where R$^3$ is —(C=O)OR$^6$, R$^6$ is —$(C_1$ to $C_3)$alkylaryl; or a pharmaceutically acceptable salt thereof.

2. A compound of the formula

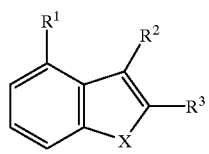

I

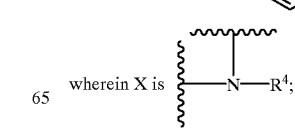

wherein X is —N—R$^4$;

-continued $R^1$ is a group of the formula

II $R^2$ is selected from hydrogen, ($C_1$ to $C_6$)alkyl; —($C_1$ to $C_3$)alkylaryl, —($C_1$ to $C_3$)alkylheteroaryl, —NH(C=O)$R^6$, —(C=O)NH$R^6$, —O(C=O)$R^6$, —(C=O)O$R^6$, —(C=O)$R^6$, O$R^6$, —SO$_n$$R^6$, —NHSO$_n$$R^6$, —SO$_n$NH$R^6$, aryl, and heteroaryl;

$R^3$ is —(C=O)NH$R^6$, —O(C=O)$R^6$ or $R^2$ and $R^3$ may optionally be taken together to form a group of the formula —(C=O)NH—(CH$R^6$)—CH$_2$—;

$R^4$ is hydrogen;

$R^5$ is hydrogen, ($C_1$ to $C_3$)alkyl, or —($C_1$ to $C_3$)alkylaryl;

$R^6$ is hydrogen, ($C_1$ to $C_6$)alkyl, —($C_1$ to $C_3$)alkylaryl, —($C_1$ to $C_3$)alkylheteroaryl, aryl, heteroaryl, and —(CH$_2$)—Y—$R^7$;

$R^7$ is hydrogen, ($C_1$ to $C_6$)alkyl, —($C_1$ to $C_3$)alkylaryl, —($C_1$ to $C_3$)alkylheteroaryl, —(C=O)NH$R^8$, —(C=O)O$R^8$, —(C=O)$R^8$, —O$R^8$, —SO$_n$$R^8$, —SO$_n$NH$R^8$, aryl, and heteroaryl;

$R^8$ is hydrogen, ($C_1$ to $C_3$)alkyl, aryl, heteroaryl, —($C_1$ to $C_3$)alkylaryl and —($C_1$ to $C_3$)alkylheteroaryl;

Y is oxygen, SO$_n$—, or NH;

a and n are independently 0, 1, or 2;

and said heteroaryl groups and the heteroaryl moieties of said alkylheteroaryl groups are selected from pyridyl and indolyl;

and said heteroaryl groups and the heteroaryl moieties of said alkylheteroaryl groups may optionally be substituted with from one to three substituents independently selected from ($C_1$ to $C_4$)alkyl, halogen, hydroxy, cyano, carboxamido, nitro, ($C_1$ to $C_4$)alkoxy —($C_1$ to $C_3$)alkylaryl, —($C_1$ to $C_3$)alkylheteroaryl, aryl, heteroaryl, and —(CH$_2$)—Y—$R^7$;

and said aryl groups and the aryl moieties of said alkylaryl groups are phenyl and may optionally be substituted with from one to three substituents independently selected from ($C_1$ to $C_4$)alkyl, halogen, hydroxy, cyano, carboxamido, nitro, and ($C_1$ to $C_4$)alkoxy;

or a pharmaceutically acceptable salt thereof.

3. A compound according to claim 2 wherein $R^5$ is hydrogen or —CH$_3$.

4. A compound selected from:
4-methyl-1-(2-(pyrid-3-yl)-1H-indol-4-yl)piperazine;
1-(2-(3-cyanophenyl)-1H-indol-4-yl)-4-methylpiperazine;
5-(4-methylpiperazin-1-yl)-1-oxo-1,2,3,4-tetrahydro-9H-pyrido[3,4-b]indole;
1-(2-aminocarbonyl-1H-indol-4-yl)-4-methylpiperazine;
4-methyl-1-(2-phenylmethylaminocarbonyl-1H-indol-4-yl) piperazine;
1-[2-(2-(indol-3-yl)ethylaminocarbonyl)-1H-indol-4-yl]-4-methylpiperazine;
1-(2-(4-chlorophenylaminocarbonyl)-1H-indol-4-yl)-4-methylpiperazine;
1-(2-(4-chlorophenylmethylaminocarbonyl)-1H-indol-4-yl)-4-methylpiperazine;
4-methyl-1-(2-(pyrid-3-ylmethyl)aminocarbonyl-1H-indol-4-yl)piperazine;
4-methyl-1-(2-(pyrid-2-ylmethyl)aminocarbonyl-1H-indol-4-yl)piperazine;
4-methyl-1-(2-(pyrid-4-ylmethyl)aminocarbonyl-1H-indol-4-yl)piperazine;
4-methyl-1-(2-(2-phenylethylaminocarbonyl)-1H-indol-4-yl)piperazine;
1-(2-(benzhydrylaminocarbonyl)-1H-indol-4-yl)-4-methylpiperazine;
4-methyl-1-(2-(1R-phenylethylaminocarbonyl)-1H-indol-4-yl)piperazine;
4-methyl-1-(2-(1S-phenylethylaminocarbonyl)-1H-indol-4-yl)piperazine;
4-methyl-1-(2-(methylaminocarbonyl)-1H-indol-4-yl) piperazine;
1-(2-(3,4-dichlorophenylmethylaminocarbonyl)-1H-indol-4-yl)-4-methylpiperazine;
1-(2-(4-chlorophenylmethoxycarbonyl)-1H-indol-4-yl)-4-methylpiperazine;
1-(2-(4-methoxyphenylmethoxycarbonyl)-1H-indol-4-yl)-4-methylpiperazine;
1-(2-(4-methoxyphenylmethylaminocarbonyl)-1H-indol-4-yl)-4-methylpiperazine;
1-(2-(4-fluorophenylmethylaminocarbonyl)-1H-indol-4-yl)-4-methylpiperazine;
4-methyl-1-(2-(4-trifluoromethylphenylmethoxycarbonyl)-1H-indol-4-yl)piperazine;
1-(2-(4-bromophenylmethylaminocarbonyl)-1H-indol-4-yl)-4-methylpiperazine;
1-(2-(4-aminosulfonylphenylmethylaminocarbonyl)-1H-indol-4-yl)-4-methylpiperazine;
1-(2-(4-butoxyphenylmethylaminocarbonyl)-1H-indol-4-yl)-4-methylpiperazine;
4-methyl-1-(2-(4-biphenylmethoxycarbonyl)-1H-indol-4-yl)piperazine;
4-methyl-1-(2-(4-phenylmethoxyphenylmethoxycarbonyl)-1H-indol-4-yl)piperazine;
1-(2-(4-ethoxyphenylmethoxycarbonyl)-1H-indol-4-yl)-4-methylpiperazine;
and the pharmaceutically acceptable salts thereof.

5. A compound according to claim 2 wherein $R^3$ is —(C=O)NH$R^6$.

6. A compound according to claim 2 wherein $R^3$ is —(C=O)O$R^6$.

7. A compound according to claim 2 wherein $R^2$ together with $R^3$ forms a group of the structure —(C=O)NH—(CH$R^6$)—CH$_2$—.

8. A compound according to claim 5 wherein $R^4$ is hydrogen and $R^5$ is hydrogen or —CH$_3$.

9. A compound according to claim 7 wherein $R^4$ is hydrogen and $R^5$ is hydrogen or —CH$_3$.

10. A compound selected from:
1-(2-aminocarbonyl-1H-indol-4-yl)-4-methylpiperazine;
4-methyl-1-(2-phenylmethylaminocarbonyl-1H-indol-4-yl) piperazine;
1-[2-(2-(indol-3-yl)ethylaminocarbonyl)-1H-indol-4-yl]-4-methylpiperazine;
1-(2-(4-chlorophenylaminocarbonyl)-1H-indol-4-yl)-4-methylpiperazine;
1-(2-(4-chlorophenylmethylaminocarbonyl)-1H-indol-4-yl)-4-methylpiperazine;
4-methyl-1-(2-(pyrid-3-ylmethyl)aminocarbonyl-1H-indol-4-yl)piperazine;
4-methyl-1-(2-(pyrid-2-ylmethyl)aminocarbonyl-1H-indol-4-yl)piperazine;
4-methyl-1-(2-(pyrid-4-ylmethyl)aminocarbonyl-1H-indol-4-yl)piperazine;
1-(2-(4-chlorophenylmethylaminocarbonyl)-1-methylindol-4-yl)-4-methylpiperazine;

4-methyl-1-(2-(2-phenylethylaminocarbonyl)-1H-indol-4-yl)piperazine;
1-(2-(benzhydrylaminocarbonyl)-1H-indol-4-yl)-4-methylpiperazine;
4-methyl-1-(2-(1R-phenylethylaminocarbonyl)-1H-indol-4-yl)piperazine;
4-methyl-1-(2-(1S-phenylethylaminocarbonyl)-1H-indol-4-yl)piperazine;
4-methyl-1-(2-(methylaminocarbonyl)-1H-indol-4-yl)piperazine;
1-(2-(3,4-dichlorophenylmethylaminocarbonyl)-1H-indol-4-yl)-4-methylpiperazine;
1-(2-(4-methoxyphenylmethylaminocarbonyl)-1H-indol-4-yl)-4-methylpiperazine;
4-methyl-1-(2-(4-trifluoromethylphenylmethoxycarbonyl)-1H-indol-4-yl)piperazine;
1-(2-(4-bromophenylmethylaminocarbonyl)-1H-indol-4-yl)-4-methylpiperazine;
1-(2-(4-aminosulfonylphenylmethylaminocarbonyl)-1H-indol-4-yl)-4-methylpiperazine;
1-(2-(4-butoxyphenylmethylaminocarbonyl)-1H-indol-4-yl)-4-methylpiperazine; and
the pharmaceutically acceptable salts thereof.

11. The compound of claim 2 wherein $R^5$ is hydrogen or $(C_1–C_3)$ alkyl.

12. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

13. A method for treating a condition selected from depression and anxiety comprising administering to a mammal requiring such treatment or prevention an amount of a compound according to claim 1 effective in treating or preventing such condition.

* * * * *